United States Patent
Kimoto et al.

(10) Patent No.: US 6,969,600 B2
(45) Date of Patent: *Nov. 29, 2005

(54) CARBONYL REDUCTASE, METHOD FOR PRODUCING SAID ENZYME, DNA ENCODING SAID ENZYME, AND METHOD FOR PRODUCING ALCOHOL USING SAID ENZYME

(75) Inventors: Norihiro Kimoto, Tsukuba (JP); Hiroaki Yamamoto, Tsukuba (JP); Kazuya Mitsuhashi, Tsukuba (JP)

(73) Assignee: Daicel Chemical Industries, Ltd., Osaka (JP)

( * ) Notice: Subject to any disclaimer, the term of this patent is extended or adjusted under 35 U.S.C. 154(b) by 831 days.

This patent is subject to a terminal disclaimer.

(21) Appl. No.: 09/855,309

(22) Filed: May 14, 2001

(65) Prior Publication Data

US 2004/0197773 A1 Oct. 7, 2004

Related U.S. Application Data

(62) Division of application No. 09/468,738, filed on Dec. 21, 1999, now Pat. No. 6,312,933.

(30) Foreign Application Priority Data

Dec. 21, 1998 (JP) ............................................ 10-363130
Jun. 17, 1999 (JP) ............................................ 11-171160

(51) Int. Cl.[7] ............................ C12N 9/02; C12Q 1/26; C12P 21/06; C07H 21/04
(52) U.S. Cl. ........................ 435/189; 435/25; 435/69.1; 435/252.3; 536/23.2
(58) Field of Search ......................... 435/189, 25, 69.1, 435/190, 440; 536/23.2

(56) References Cited

FOREIGN PATENT DOCUMENTS

EP  0 927 755 A2   7/1999
EP  0 967 271 A1  12/1999

OTHER PUBLICATIONS

Kita et al., "Cloning, Overexpression, and Mutagenesis of the . . . ," Applied and Environmental Microbiology, vol. 65, No. 12, pp. 5207–5211, 1999.

Bradshaw et al., "A *Pseudomonas* sp. Alcohol Dehydrogenase with Broad . . . ," J. Org. Chem., vol. 57, pp. 1526–1532, 1992.

Shieh et al., "Stereochemical Control of Yeast . . . ," J. Am. Chem. Soc., vol. 107, pp. 2993–2994, 1985.

Patel et al., "Stereoselective reduction of . . . ," Enzyme Microb. Technol., vol. 14, pp. 731–738, 1992.

Peters et al. "A novel NADH–dependent carbonyl reductase with an extremely broad substrate range from *Candidan parapsilosis*: purification and characterization," Enzyme Microb. Technol., 15(11):pp. 950–958.

*Primary Examiner*—Manjunath Rao
*Assistant Examiner*—Yong Pak
(74) *Attorney, Agent, or Firm*—Fish & Richardson P.C.

(57) ABSTRACT

A novel carbonyl reductase useful for producing alcohol, particularly derivatives of (S)-4-halo-3-hydroxybutyrate ester, is provided. A novel carbonyl reductase derived from *Kluyveromyces aestuarii* and the nucleic acid encoding the enzyme are provided. The carbonyl reductase has excellent reductase activity and stereoselectivity. The carbonyl reductase reduces ketone to produce alcohol. It can be particularly advantageous when used in industrial production of (S)-4-halo-3-hydroxybutyrate ester.

1 Claim, 5 Drawing Sheets

SEQUENCE LISTING

<160> NUMBER OF SEQ ID NOS: 29

<210> SEQ ID NO 1
<211> LENGTH: 879
<212> TYPE: DNA

<213> ORGANISM: Kluyveromyces aestuarii

<400> SEQUENCE: 1

```
atgacgtttc agcattttt aagaggtgga ttagaagata aaacagttcc tcaggagcca      60
ccgaaggagc aatatcccga tggtgttaat tacttgagct tgttcagtca gaaagggaaa     120
ttgacagtta tcactggtgg agcaggagcc attggcggag ctctgtgtga gggatttgcg     180
tcctgtggat ctgacgttgt cattttagat tacaaataca gtcctgaatt gtcatcagtt     240
ttggaatcta ggtatggagt gaggtcgaaa agctatcagg tcgacattac gagttcagaa     300
gacgtgaaac ttgttgttgc aaagatttta gaagattttc ctgatcgcga tatcaataca     360
tttgttgcta atgcaggtat tgcatggacc aacggttcca ttttgaacga aaacgcgacg     420
ccagatgtgt ggaaacgtgt tatggatgtg aacgtgcaag gaacttatca ttgtgcgaaa     480
tatgtggcag aagtgttcaa acaacagggc catggtaatc tgattttgac tgcgtcgatg     540
tcaagttata taagcaacgt tcccaactac caaacatgtt ataatgcctc taaagcggcc     600
gtcagacata tggcaaaggg atttgctgtt gaattcgccc atttgacaaa ccccgcaggt     660
aaaatcagat gcaattcggt ttcacctggt tacactgaca ccgcactttc agcttttgtt     720
ccggtcgaac agcgcgctca gtggtgggga ttgactccta tgggtcgcga agcattacca     780
caagagctag tcggagccta cttgtatttg gcatctgacg ctgcatcatt cacaaatgga     840
tgtgatattc aagtagacgg tgggtacact tgcgtttga                            879
```

<210> SEQ ID NO 2
<211> LENGTH: 292
<212> TYPE: PRT
<213> ORGANISM: Kluyveromyces aestuarii

<400> SEQUENCE: 2

```
Met Thr Phe Gln His Phe Leu Arg Gly Gly Leu Glu Asp Lys Thr Val
  1               5                  10                  15

Pro Gln Glu Pro Pro Lys Glu Gln Tyr Pro Asp Gly Val Asn Tyr Leu
             20                  25                  30

Ser Leu Phe Ser Gln Lys Gly Lys Leu Thr Val Ile Thr Gly Gly Ala
         35                  40                  45

Gly Ala Ile Gly Gly Ala Leu Cys Glu Gly Phe Ala Ser Cys Gly Ser
     50                  55                  60

Asp Val Val Ile Leu Asp Tyr Lys Tyr Ser Pro Glu Leu Ser Ser Val
 65                  70                  75                  80

Leu Glu Ser Arg Tyr Gly Val Arg Ser Lys Ser Tyr Gln Val Asp Ile
                 85                  90                  95

Thr Ser Ser Glu Asp Val Lys Leu Val Val Ala Lys Ile Leu Glu Asp
            100                 105                 110

Phe Pro Asp Arg Asp Ile Asn Thr Phe Val Ala Asn Ala Gly Ile Ala
        115                 120                 125

Trp Thr Asn Gly Ser Ile Leu Asn Glu Asn Ala Thr Pro Asp Val Trp
    130                 135                 140

Lys Arg Val Met Asp Val Asn Val Gln Gly Thr Tyr His Cys Ala Lys
145                 150                 155                 160

Tyr Val Ala Glu Val Phe Lys Gln Gln Gly His Gly Asn Leu Ile Leu
                165                 170                 175

Thr Ala Ser Met Ser Ser Tyr Ile Ser Asn Val Pro Asn Tyr Gln Thr
            180                 185                 190

Cys Tyr Asn Ala Ser Lys Ala Ala Val Arg His Met Ala Lys Gly Phe
```

-continued

```
                    195                 200                 205
Ala Val Glu Phe Ala His Leu Thr Asn Pro Ala Gly Lys Ile Arg Cys
    210                 215                 220

Asn Ser Val Ser Pro Gly Tyr Thr Asp Thr Ala Leu Ser Ala Phe Val
225                 230                 235                 240

Pro Val Glu Gln Arg Ala Gln Trp Trp Gly Leu Thr Pro Met Gly Arg
                245                 250                 255

Glu Ala Leu Pro Gln Glu Leu Val Gly Ala Tyr Leu Tyr Leu Ala Ser
            260                 265                 270

Asp Ala Ala Ser Phe Thr Asn Gly Cys Asp Ile Gln Val Asp Gly Gly
        275                 280                 285

Tyr Thr Cys Val
    290

<210> SEQ ID NO 3
<211> LENGTH: 10
<212> TYPE: PRT
<213> ORGANISM: Kluyveromyces aestuarii

<400> SEQUENCE: 3

Thr Phe Gln His Phe Leu Arg Gly Gly Leu
1               5                   10

<210> SEQ ID NO 4
<211> LENGTH: 10
<212> TYPE: PRT
<213> ORGANISM: Kluyveromyces aestuarii

<400> SEQUENCE: 4

Tyr Ser Pro Glu Leu Ser Ser Val Leu Glu
1               5                   10

<210> SEQ ID NO 5
<211> LENGTH: 10
<212> TYPE: PRT
<213> ORGANISM: Kluyveromyces aestuarii

<400> SEQUENCE: 5

Gly Phe Ala Val Glu Phe Ala His Leu Thr
1               5                   10

<210> SEQ ID NO 6
<211> LENGTH: 35
<212> TYPE: DNA
<213> ORGANISM: Artificial Sequence
<220> FEATURE:
<223> OTHER INFORMATION: Artificially Synthesized Primer Sequence

<400> SEQUENCE: 6
gacggatcca cwttycarca yttyytragr ggwgg                          35

<210> SEQ ID NO 7
<211> LENGTH: 35
<212> TYPE: DNA
<213> ORGANISM: Artificial Sequence
<220> FEATURE:
<223> OTHER INFORMATION: Artificially Synthesized Primer Sequence

<400> SEQUENCE: 7
gtgaagcttc cwccyctyar raartgytgr aawgt                          35

<210> SEQ ID NO 8
```

```
<211> LENGTH: 38
<212> TYPE: DNA
<213> ORGANISM: Artificial Sequence
<220> FEATURE:
<223> OTHER INFORMATION: Artificially Synthesized Primer Sequence

<400> SEQUENCE: 8
gacggatcct aytstccwga rttrtsttst gtwttrga                               38

<210> SEQ ID NO 9
<211> LENGTH: 38
<212> TYPE: DNA
<213> ORGANISM: Artificial Sequence
<220> FEATURE:
<223> OTHER INFORMATION: Artificially Synthesized Primer Sequence

<400> SEQUENCE: 9
gtgaagcttt cyaawacasa asayaaytcw ggasarta                               38

<210> SEQ ID NO 10
<211> LENGTH: 32
<212> TYPE: DNA
<213> ORGANISM: Artificial Sequence
<220> FEATURE:
<223> OTHER INFORMATION: Artificially Synthesized Primer Sequence
<221> NAME/KEY: misc_feature
<222> LOCATION: (0)...(0)
<223> OTHER INFORMATION: n = A, T, G, or C

<400> SEQUENCE: 10
gacggatccg gwttygcwgt wgarttygcn ca                                     32

<210> SEQ ID NO 11
<211> LENGTH: 32
<212> TYPE: DNA
<213> ORGANISM: Artificial Sequence
<220> FEATURE:
<223> OTHER INFORMATION: Artificially Synthesized Primer Sequence
<221> NAME/KEY: misc_feature
<222> LOCATION: (0)...(0)
<223> OTHER INFORMATION: n = A, T, G, or C

<400> SEQUENCE: 11
gtgaagcttt gngcraaytc wacwgcraaw cc                                     32

<210> SEQ ID NO 12
<211> LENGTH: 254
<212> TYPE: DNA
<213> ORGANISM: Kluyveromyces aestuarii

<400> SEQUENCE: 12
ggatccactt tccagcattt cttgagagga ggattagaag ataaaacagt tcctcaggag        60
ccaccgaagg agcaatatcc cgatggtgtt aattacttga gcttgttcag tcagaaaggg       120
aaattgacag ttatcactgg tggagcagga gccattggcg gagctctgtg tgagggattt       180
gcgtcctgtg gatctgacgt tgtcatttta gattacaaat actctcctga attatcttct      240
gtattagaaa gctt                                                        254

<210> SEQ ID NO 13
<211> LENGTH: 650
<212> TYPE: DNA
<213> ORGANISM: Kluyveromyces aestuarii

<400> SEQUENCE: 13
ggatccactt ttcagcactt tctgaggga ggattagaag ataaaacagt tcctcaggag         60
```

-continued

```
ccaccgaagg agcaatatcc cgatggtgtt aattacttga gcttgttcag tcagaaaggg      120
aaattgacag ttatcactgg tggagcagga gccattggcg gagctctgtg tgagggattt      180
gcgtcctgtg gatctgacgt tgtcatttta gattacaaat acagtcctga attgtcatca      240
gttttggaat ctaggtatgg agtgaggtcg aaaagctatc aggtcgacat tacgagttca      300
gaagacgtga aacttgttgt tgcaaagatt ttagaagatt ttcctgatcg cgatatcaat      360
acatttgttg ctaatgcagg tattgcatgg accaacggtt ccattttgaa cgaaaacgcg      420
acgccagatg tgtggaaacg tgttatggat gtgaacgtgc aaggaactta tcattgtgcg      480
aaatatgtgg cagaagtgtt caaacaacag ggccatggta atctgatttt gactgcgtcg      540
atgtcaagtt atataagcaa cgttcccaac taccaaacat gttataatgc ctctaaagcg      600
gccgtcagac atatggcaaa gggttttgca gtagagttcg cacaaagctt                 650
```

<210> SEQ ID NO 14
<211> LENGTH: 437
<212> TYPE: DNA
<213> ORGANISM: Kluyveromyces aestuarii

<400> SEQUENCE: 14

```
ggatcctaat gtccagagtt atgttgtgta ttggaatcta ggtatggagt gaggtcgaaa       60
agctatcagg tcgacattac gagttcagaa gacgtgaaac ttgttgttgc aaagatttta     120
gaagattttc ctgatcgcga tatcaataca tttgttgcta atgcaggtat tgcatggacc     180
aacggttcca ttttgaacga aaacgcgacg ccagatgtgt ggaaacgtgt tatggatgtg     240
aacgtgcaag gaacttatca ttgtgcgaaa tatgtggcag aagtgttcaa acaacagggc     300
catggtaatc tgattttgac tgcgtcgatg tcaagttata taagcaacgt tcccaactac     360
caaacatgtt ataatgcctc taaagcggcc gtcagacata tggcaagggg attcgcagta     420
gaattcgctc aaagctt                                                    437
```

<210> SEQ ID NO 15
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 15

```
tcggtggctc ctgaggaac                                                   19
```

<210> SEQ ID NO 16
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 16

```
acatgttata atgcctctaa agc                                              23
```

<210> SEQ ID NO 17
<211> LENGTH: 1787
<212> TYPE: DNA
<213> ORGANISM: Kluyveromyces aestuarii
<220> FEATURE:
<221> NAME/KEY: misc_feature
<222> LOCATION: (0)...(0)
<223> OTHER INFORMATION: n = A, T, G, or C

```
<400> SEQUENCE: 17
aggagtggca cattcaccgt gttgtgggag gtaagcaacc gtcagaaccc gccgtcgggt      60
gcacwtwmcy tmaaaamgaw atmgtatgrg gkrrtsacgt acacawygta ttwagttygc     120
maagacaagg cgraatagat gacgracgtt ggctgtaaat gtcggggggac naaatagatg    180 caaatawtws wgmnaymwww gkmmymkwyn ttttttaaat agcctggtta actacggcag     240
catgggctcg gtggtaggga agaacaatt agtctatatt taggagagag gtataaataa     300
atgaaaagat gcatatggaa attggataat ttcacacaat ttacgatgga ctgatctgta    360
catgaactct ttgatatgta tcttatgtta tttttccttt aagcgacttc atagtggttt    420
cgggcctcgt tcatcggaga gctagctttg cacctgagtt tgggtttaga cacactataa    480
gaagagttta aagtctagga agtattcaaa aaataaagta aaagtcgcaa tgacgtttca    540 gcattttta  agaggtggat tagaagataa  aacagttcct caggagccac cgaaggagca    600
atatcccgat ggtgttaatt acttgagctt gttcagtcag aaagggaaat tgacagttat    660
cactggtgga gcaggagcca ttggcggagc tctgtgtgag ggatttgcgt cctgtggatc    720
tgacgttgtc attttagatt acaaatacag tcctgaattg tcatcagttt tggaatctag    780
gtatggagtg aggtcgaaaa gctatcaggt cgacattacg agttcagaag acgtgaaact    840
tgttgttgca aagattttag aagattttcc tgatcgcgat atcaatacat tgttgctaa    900 tgcaggtatt gcatggacca acggttccat tttgaacgaa aacgcgacgc cagatgtgtg    960
gaaacgtgtt atggatgtga acgtgcaagg aacttatcat tgtgcgaaat atgtggcaga   1020
agtgttcaaa caacagggcc atggtaatct gattttgact gcgtcgatgt caagttatat   1080
aagcaacgtt cccaactacc aaacatgtta taatgcctct aaagcggccg tcagacatat   1140
ggcaaaggga tttgctgttg aattcgccca tttgacaaac cccgcaggta aaatcagatg   1200
caattcggtt tcacctggtt acactgacac cgcactttca gcttttgttc cggtcgaaca   1260
gcgcgctcag tggtggggat tgactcctat gggtcgcgaa gcattaccac aagagcyagt   1320
cggagcctac ttgtatttgg catctgacgc tgcatcattc acaaatggat gtgatattca   1380
agtagacggt gggtacactt gcgtttgatt ttgaacaaat ccaaatcaac ggttatttac   1440
cgttatanaa tttggctama agtwttanca natnyancga attattcama rawmwtttyc   1500
ccccanagtt gcyyymymyc ycaaraatga cmttgttaaw mmsywtgtwr aaacacggca   1560
gttyccyatg gtattgattc gatgagttac aactttcatc acgtaaaaat gccagaaaaa   1620
aaaaggttgt taatcaaata gacacgcttt cgaaaccatg catcaaacgg tcctaaacag   1680
aacaatacag gacactgtgc agcatggtat cggcaatcca aagcttcata tccacaagac   1740
tcatcaacga agtcactccc agtcacattt tttggattta tgcgatt               1787

<210> SEQ ID NO 18
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 18
tcaggatcca acaatgactt ttcagcattt tttaag                              36

<210> SEQ ID NO 19
<211> LENGTH: 31
<212> TYPE: DNA
<213> ORGANISM: Artificial Sequence
```

<220> FEATURE:
<223> OTHER INFORMATION: Artificially Synthesized Primer Sequence

<400> SEQUENCE: 19
tgttctagat taaacgcaag tgtacccacc g        31

<210> SEQ ID NO 20
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 20
tctgtatcag gctgaaaatc ttc        23

<210> SEQ ID NO 21
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 21
atatattaat gtatcgatta aataaggag        29

<210> SEQ ID NO 22
<211> LENGTH: 891
<212> TYPE: DNA
<213> ORGANISM: Kluyveromyces aestuarii

<400> SEQUENCE: 22
atggatccaa caatgacgtt tcagcatttt ttaagaggtg gattagaaga taaaacagtt        60
cctcaggagc caccgaagga gcaatatccc gatggtgtta attacttgag cttgttcagt       120
cagaaaggga aattgacagt tatcactggt ggagcaggag ccattggcgg agctctgtgt       180
gagggatttg cgtcctgtgg atctgacgtt gtcattttag attacaaata cagtcctgaa       240
ttgtcatcag ttttggaatc taggtatgga gtgaggtcga aaagctatca ggtcgacatt       300
acgagttcag aagacgtgaa acttgttgtt gcaaagattt agaagatttt cctgatcgc        360
gatatcaata catttgttgc taatgcaggt attgcatgga ccaacggttc cattttgaac       420
gaaaacgcga cgccagatgt gtggaaacgt gttatggatg tgaacgtgca aggaacttat       480
cattgtgcga aatatgtggc agaagtgttc aaacaacagg gccatggtaa tctgattttg       540
actgcgtcga tgtcaagtta taagcaac gttcccaact accaaacatg ttataatgcc       600
tctaaagcgg ccgtcagaca tatggcaaag ggatttgctg ttgaattcgc ccatttgaca       660
aaccccgcag gtaaaatcag atgcaattcg gtttcacctg gttacactga caccgcactt       720
tcagcttttg ttccggtcga acagcgcgct cagtggtggg gattgactcc tatgggtcgc       780
gaagcattac acaagagct agtcggagcc tacttgtatt ggcatctga cgctgcatca       840
ttcacaaatg gatgtgatat tcaagtagac ggtgggtaca cttgcgttta a                891

<210> SEQ ID NO 23
<211> LENGTH: 296
<212> TYPE: PRT
<213> ORGANISM: Kluyveromyces aestuarii

<400> SEQUENCE: 23

Met Asp Pro Thr Met Thr Phe Gln His Phe Leu Arg Gly Gly Leu Glu
 1               5                  10                  15

```
Asp Lys Thr Val Pro Gln Glu Pro Lys Glu Gln Tyr Pro Asp Gly
             20                  25                  30

Val Asn Tyr Leu Ser Leu Phe Ser Gln Lys Gly Lys Leu Thr Val Ile
         35                  40                  45

Thr Gly Gly Ala Gly Ala Ile Gly Gly Ala Leu Cys Glu Gly Phe Ala
 50                  55                  60

Ser Cys Gly Ser Asp Val Val Ile Leu Asp Tyr Lys Tyr Ser Pro Glu
 65                  70                  75                  80

Leu Ser Ser Val Leu Glu Ser Arg Tyr Gly Val Arg Ser Lys Ser Tyr
             85                  90                  95

Gln Val Asp Ile Thr Ser Ser Glu Asp Val Lys Leu Val Ala Lys
             100                 105                 110

Ile Leu Glu Asp Phe Pro Asp Arg Asp Ile Asn Thr Phe Val Ala Asn
             115                 120                 125

Ala Gly Ile Ala Trp Thr Asn Gly Ser Ile Leu Asn Glu Asn Ala Thr
 130                 135                 140

Pro Asp Val Trp Lys Arg Val Met Asp Val Asn Val Gln Gly Thr Tyr
145                 150                 155                 160

His Cys Ala Lys Tyr Val Ala Glu Val Phe Lys Gln Gln Gly His Gly
             165                 170                 175

Asn Leu Ile Leu Thr Ala Ser Met Ser Ser Tyr Ile Ser Asn Val Pro
             180                 185                 190

Asn Tyr Gln Thr Cys Tyr Asn Ala Ser Lys Ala Ala Val Arg His Met
             195                 200                 205

Ala Lys Gly Phe Ala Val Glu Phe Ala His Leu Thr Asn Pro Ala Gly
 210                 215                 220

Lys Ile Arg Cys Asn Ser Val Ser Pro Gly Tyr Thr Asp Thr Ala Leu
225                 230                 235                 240

Ser Ala Phe Val Pro Val Glu Gln Arg Ala Gln Trp Trp Gly Leu Thr
             245                 250                 255

Pro Met Gly Arg Glu Ala Leu Pro Gln Glu Leu Val Gly Ala Tyr Leu
             260                 265                 270

Tyr Leu Ala Ser Asp Ala Ala Ser Phe Thr Asn Gly Cys Asp Ile Gln
             275                 280                 285

Val Asp Gly Gly Tyr Thr Cys Val
             290                 295

<210> SEQ ID NO 24
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 24
aattctcgag taatctagag gaattctaaa a                               31

<210> SEQ ID NO 25
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 25
ctagttttag aattcctcta gattactcga g                               31
```

<210> SEQ ID NO 26
<211> LENGTH: 35
<212> TYPE: DNA
<213> ORGANISM: Artificial Sequence
<220> FEATURE:
<223> OTHER INFORMATION: Artificially Synthesized Primer Sequence

<400> SEQUENCE: 26
gaggaattca tacatgtatc cagatttaaa aggaa    35

<210> SEQ ID NO 27
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 27
ggtaagcttt cattaaccgc ggcctgcctg    30

<210> SEQ ID NO 28
<211> LENGTH: 786
<212> TYPE: DNA
<213> ORGANISM: Bacillus subtilis

<400> SEQUENCE: 28
atgtatccag atttaaaagg aaaagtcgtc gctattacag agctgcttc agggctcgga    60 aaggcgatgg ccattcgctt cggcaaggag caggcaaaag tggttatcaa ctattatagt    120
aataaacaag atccgaacga ggtaaaagaa gaggtcatca aggcgggcgg tgaagctgtt    180
gtcgtccaag gagatgtcac gaaagaggaa gatgtaaaaa atatcgtgca acggcaatt    240 aaggagttcg gcacactcga tattatgatt aataatgccg gtcttgaaaa tcctgtgcca    300
tctcacgaaa tgccgctcaa ggattgggat aaagtcatcg gcacgaactt aacgggtgcc    360
tttttaggaa gccgtgaagc gattaaatat ttcgtagaaa acgatatcaa gggaaatgtc    420
attaacatgt ccagtgtgca cgaagtgatt ccttggccgt tatttgtcca ctatgcggca    480
agtaaaggcg ggataaagct gatgacagaa acattagcgt tggaatacgc gccgaagggc    540
attcgcgtca ataatattgg gccaggtgcg atcaacacgc caatcaatgc tgaaaaattc    600
gctgacccta acagaaaagc tgatgtagaa agcatgattc caatgggata tatcggcgaa    660
ccggaggaga tcgccgcagt agcagcctgg cttgcttcga aggaagccag ctacgtcaca    720
ggcatcacgt tattcgcgga cggcggtatg acacaatatc cttcattcca ggcaggccgc    780
ggttaa    786

<210> SEQ ID NO 29
<211> LENGTH: 261
<212> TYPE: PRT
<213> ORGANISM: Bacillus subtilis

<400> SEQUENCE: 29

Met Tyr Pro Asp Leu Lys Gly Lys Val Val Ala Ile Thr Gly Ala Ala
  1               5                  10                  15

Ser Gly Leu Gly Lys Ala Met Ala Ile Arg Phe Gly Lys Glu Gln Ala
                 20                  25                  30

Lys Val Val Ile Asn Tyr Tyr Ser Asn Lys Gln Asp Pro Asn Glu Val
             35                  40                  45

Lys Glu Glu Val Ile Lys Ala Gly Gly Glu Ala Val Val Val Gln Gly
         50                  55                  60

```
Asp Val Thr Lys Glu Glu Asp Val Lys Asn Ile Val Gln Thr Ala Ile
 65              70                  75                  80

Lys Glu Phe Gly Thr Leu Asp Ile Met Ile Asn Asn Ala Gly Leu Glu
             85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
            245                 250                 255

Gln Ala Gly Arg Gly
            260
```

CARBONYL REDUCTASE, METHOD FOR PRODUCING SAID ENZYME, DNA ENCODING SAID ENZYME, AND METHOD FOR PRODUCING ALCOHOL USING SAID ENZYME

This application is a divisional of U.S. patent application Ser. No. 09/468,738, filed Dec. 21, 1999 now issued as U.S. Pat. No. 6,312,933, which claims priority from Japanese Patent Application Nos. 10/363130, filed Dec. 21, 1998, and 11/171160, filed Jun. 17, 1999.

FIELD OF INVENTION

The present invention relates to a novel, reduced beta-nicotinamide adenine dinucleotide-dependent carbonyl reductase that is useful for producing alcohol, particularly (S)-4-halo-3-hydroxybutyrate ester; DNA encoding said enzyme; a method for producing said enzyme; and a method for producing alcohol, particularly (S)-4-halo-3-hydroxybutyrate ester, using said enzyme.

BACKGROUND OF THE INVENTION

Asymmetric reduction methods using microorganisms such as baker's yeast to produce optically active (S)-4-halo-3-hydroxybutyrate ester (Unexamined Published Japanese Patent Application No. (JP-A) Sho 61-146191, JP-A Hei 6-209782, and so on) have been known for some time. These production methods, however, have problems that must be solved for industrial applications because the optical purity and yield of the product are low due to more than one reductases existing in microbial cells. Optically active (S)-4-halo-3-hydroxybutyrate ester is utilized as a synthetic intermediate of drugs. It is thus important in the chemical industry to determine how to produce (synthesize or resolve) optically purified antipodes of the compound.

Enzymes capable of producing (S)-4-halo-3-hydroxybutyrate ester from 4-haloacetoacetate ester are described below, and methods for synthesizing (S)-4-halo-3-hydroxybutyrate ester using these enzymes have been reported.

- 3-Hydroxysteroid dehydrogenase (JP-A Hei 1-277494)
- Glycerol dehydrogenase (Tetrahedron Lett. 29, 2453–2454 (1988))
- Alcohol dehydrogenase derived from *Pseudomonas* sp. PED (J. Org. Chem. 57, 1526–1532 (1992))
- Reductases derived from baker's yeast (D-enzyme-1, D-enzyme-2, J. Am. Chem. Soc. 107, 2993–2994 (1985))
- Aldehyde dehydrogenase 2 derived from *Sporobolomyces salmonicolor* (Abstract of 391st Meeting of the Kansai Branch of the Japan Society of Bioscience, Biotechnology, and Agrochemistry, p37 (1995))
- Ketopantothenate reductase derived from *Candida macedoniensis* (Arch. Biochem. Biophys. 294, 469–474 (1992))
- Ethyl 4-chloroacetoacetate reductase derived from *Geotrichum candidum* (Enzyme Microb. Technol. 14, 731–738 (1992))
- Carbonyl reductase derived from *Candida magnoliae* (WO98/35025)
- Carbonyl reductase derived from *Kluyveromyces lactis* (JP-A Hei 11-187869)

Most of these enzymes are reductases that require reduced nicotinamide adenine dinucleotide phosphate (NADPH) as a coenzyme. Thus, the method for synthesizing (S)-4-halo-3-hydroxybutyrate ester using these enzymes is industrially disadvantageous because it needs the addition and regeneration of expensive and chemically unstable NADPH.

3-Hydroxysteroid dehydrogenase, glycerol dehydrogenase, and alcohol dehydrogenase derived from Pseudomonas sp. PED are oxidoreductases, which catalyze not only reduction reactions using reduced nicotinamide adenine dinucleotide (NADH) as an electron donor but also oxidation (dehydrogenation) reactions. The use of these enzymes cannot produce (S)-4-halo-3-hydroxybutyrate ester in a high yield because the equilibrium of the enzymatic reaction is likely to limit the reaction rate.

SUMMARY OF THE INVENTION

An objective of this invention is to provide a carbonyl reductase that uses NADH as a coenzyme. Another objective of this invention is to provide a carbonyl reductase with excellent stereoselectivity capable of acting on a substrate, 4-haloacetoaectate ester, to produce optically active (S)-4-halo-3-hydroxybutyrate ester with high optical purity at a high yield.

Still another objective of the present invention is to isolate a DNA encoding the carbonyl reductase with desired properties and obtaining a recombinant enzyme. A further objective of the invention is to provide a method for enzymatically producing optically active (S)-4-halo-3-hydroxybutyrate ester using a novel carbonyl reductase.

Another objective of the invention is to obtain a recombinant capable of simultaneously expressing not only the desired enzyme described above but also an enzyme that reduces $NAD^+$ to NADH. It is also an objective of the invention to provide a method for enzymatically producing optically active (S)-4-halo-3-hydroxybutyrate ester using a novel carbonyl reductase, involving an enhanced regeneration system of the coenzyme using the above recombinant.

The present inventors thought that carbonyl reductases capable of utilizing NADH as an electron donor would be industrially useful since NADH is less expensive and chemically more stable than NADPH. We also thought that enzymes that reduce 4-haloacetoacetate ester to form (S)-4-halo-3-hydroxybutyrate ester but do not substantially dehydrogenate the formed (S)-4-halo-3-hydroxybutyrate ester would be useful for efficiently producing optically active (S)-4-halo-3-hydroxybutyrate ester.

The present inventors sought enzymes that meet the above requirements and found a desired enzyme from *Kluyveromyces aestuarii*.

We succeeded in isolating a novel enzyme and DNA encoding the enzyme, and in developing a method for producing alcohol using this enzyme. The present invention relates to the carbonyl reductase described below, DNA encoding said enzyme, a method for producing said enzyme, and the use of said enzyme.

1. A carbonyl reductase having the following physicochemical properties:

Reactivity

It reduces 4-haloacetoacetate ester to produce (S)-4-halo-3-hydroxybutyrate ester using reduced beta-nicotinamide adenine dinucleotide as an electron donor.

Substrate Specificity

It has high reductase activity for 4-chloroacetoacetate ester but does not substantially dehydrogenate any optical isomers of 4-halo-3-hydroxybutyrate ester and shows higher enzymatic activity when used with reduced beta-nicotinamide adenine dinucleotide as an electron donor than reduced beta-nicotinamide adenine dinucleotide phosphate.

2. The carbonyl reductase described in 1, which has additional physicochemical properties below:
Optimal pH
  5.0 to 6.0
Substrate Specificity
  It does not substantially dehydrogenate isopropanol and does not reduce acetoacetate.
Molecular Weight
  About 32,000 when determined by sodium dodecylsulfate-polyacrylamide gel electrophoresis.
3. A substantially pure polypeptide comprising the amino acid sequence represented by SEQ ID NO: 2 and having the enzymatic activity for catalyzing the reduction of 4-haloacetoacetate ester to (S)-4-halo-3-hydroxybutyrate ester using reduced beta-nicotinamide adenine dinucleotide as an electron donor.
4. A substantially pure polypeptide comprising the amino acid sequence represented by SEQ ID NO: 2 containing up to 30 conservative amino acid substitutions, and having the following enzymatic activities:
  reduces 4-haloacetoacetate ester to produce (S)-4-halo-3-hydroxybutyrate ester using reduced beta-nicotinamide adenine dinucleotide as an electron donor;
  has high reductase activity for 4-chloroacetoacetate ester but does not substantially dehydrogenate any optical isomers of 4-halo-3-hydroxy-butyrate ester; and
  shows higher enzymatic activity when used with reduced beta-nicotinamide adenine dinucleotide as an electron donor than reduced beta-nicotinamide adenine dinucleotide phosphate.
5. A substantially pure polypeptide encoded by a nucleic acid that hybridizes with the nucleic acid consisting the nucleotide sequence represented by SEQ ID NO: 1 under stringent conditions, and having the following enzymatic activities:
  reduces 4-haloacetoacetate ester to produce (S)-4-halo-3-hydroxybutyrate ester using reduced beta-nicotinamide adenine dinucleotide as an electron donor;
  has high reductase activity for 4-chloroacetoacetate ester but does not substantially dehydrogenate any optical isomers of 4-halo-3-hydroxybutyrate ester; and
  shows higher enzymatic activity when used with reduced beta-nicotinamide adenine dinucleotide as an electron donor than reduced beta-nicotinamide adenine dinucleotide phosphate.
6. The substantially pure polypeptide described in 5, comprising an amino acid sequence having at least 70% homology with the amino acid sequence represented by SEQ ID NO: 2.
7. An isolated nucleic acid encoding the polypeptide described in 3.
8. An isolated nucleic acid encoding the polypeptide described in 4.
9. An isolated nucleic acid encoding the polypeptide described in 5.
10. An isolated nucleic acid encoding the polypeptide described in 3 comprising the nucleotide sequence represented by SEQ ID NO: 1.
11. An isolated nucleic acid hybridizing with the nucleic acid consisting of the nucleotide sequence represented by SEQ ID NO: 1 under stringent conditions, and encoding a polypeptide having the following enzymatic activities:
  reduces 4-haloacetoacetate ester to produce (S)-4-halo-3-hydroxybutyrate ester using reduced beta-nicotinamide adenine dinucleotide as an electron donor;
  has high reductase activity for 4-chloroacetoacetate ester but does not substantially dehydrogenate any optical isomers of 4-halo-3-hydroxybutyrate ester; and
  shows higher enzymatic activity when used with reduced beta-nicotinamide adenine dinucleotide as an electron donor than reduced beta-nicotinamide adenine dinucleotide phosphate.
12. The nucleic acid of claim 11 comprising a nucleotide sequence having at least 70% homology with the nucleotide sequence represented by SEQ ID NO: 1.
13. A recombinant vector comprising the nucleic acid described in 7.
14. A recombinant vector comprising the nucleic acid described in 8.
15. A recombinant vector comprising the nucleic acid described in 9.
16. A transformant carrying the vector described in 13.
17. A transformant carrying the vector described in 14.
18. A transformant carrying the vector described in 15.
19. The transformant described in 16, which is a microorganism.
20. A method for producing a carbonyl reductase, the method comprising culturing the transformant described in 16.
21. A recombinant vector comprising the nucleic acid described in 7 and the nucleic acid encoding a glucose dehydrogenase.
22. The vector described in 21, wherein a glucose dehydrogenase is derived from *Bacillus subtilis*.
23. A transformant carrying the vector described in 21.
24. The transformant described in 21, which is a microorganism.
25. A method for producing the enzyme described in 1, the method comprising culturing a microorganism belonging to the genus *Kluyveromyces* and producing the enzyme described in 1.
26. The method for producing the enzyme described in 25, wherein the enzyme comprises the amino acid sequence represented by SEQ ID NO: 2.
27. The method for producing the enzyme described in 25, wherein the microorganism belonging to the genus *Kluyveromyces* is *Kluyveromyces aestuarii*.
28. A method for producing a polypeptide encoded by the nucleic acid described in 7, the method comprising culturing the transformant described in 16.
29. The method for producing the polypeptide described in 28, wherein the transformant is a microorganism.
30. A method for producing alcohol, the method comprising reacting ketone with the carbonyl reductase described in 1, microorganisms producing it, or treated microorganisms.
31. The method for producing alcohol, wherein the carbonyl reductase comprises the amino acid sequence represented by SEQ ID NO: 2.
32. The method for producing alcohol described in 30, wherein the microorganism is the transformant described in 16.
33. The method for producing alcohol described in 30, wherein ketone is a derivative of 4-haloactoacetate ester, and alcohol is a derivative of (S)-4-halo-3-hydroxybutyrate ester.
34. The method for producing alcohol described in 33, wherein the derivative of ethyl 4-haloactoacetate is 4-chloroacetoacetate ester, and alcohol is ethyl(S)-4-chloro-3-hydroxybutyrate.
35. The method for producing alcohol described in 30, the method further comprising converting oxidized beta-nicotinamide adenine dinucleotide to its reduced form.
36. The method for producing alcohol described in 35, wherein oxidized beta-nicotinamide adenine dinucleotide is reduced by a conversion of glucose to delta-gluconolactone by using a glucose dehydrogenase.

37. The method for producing alcohol described in 36, wherein glucose dehydrogenase is expressed by the transformant described in 23.

DETAILED DESCRIPTION

Figure 1:
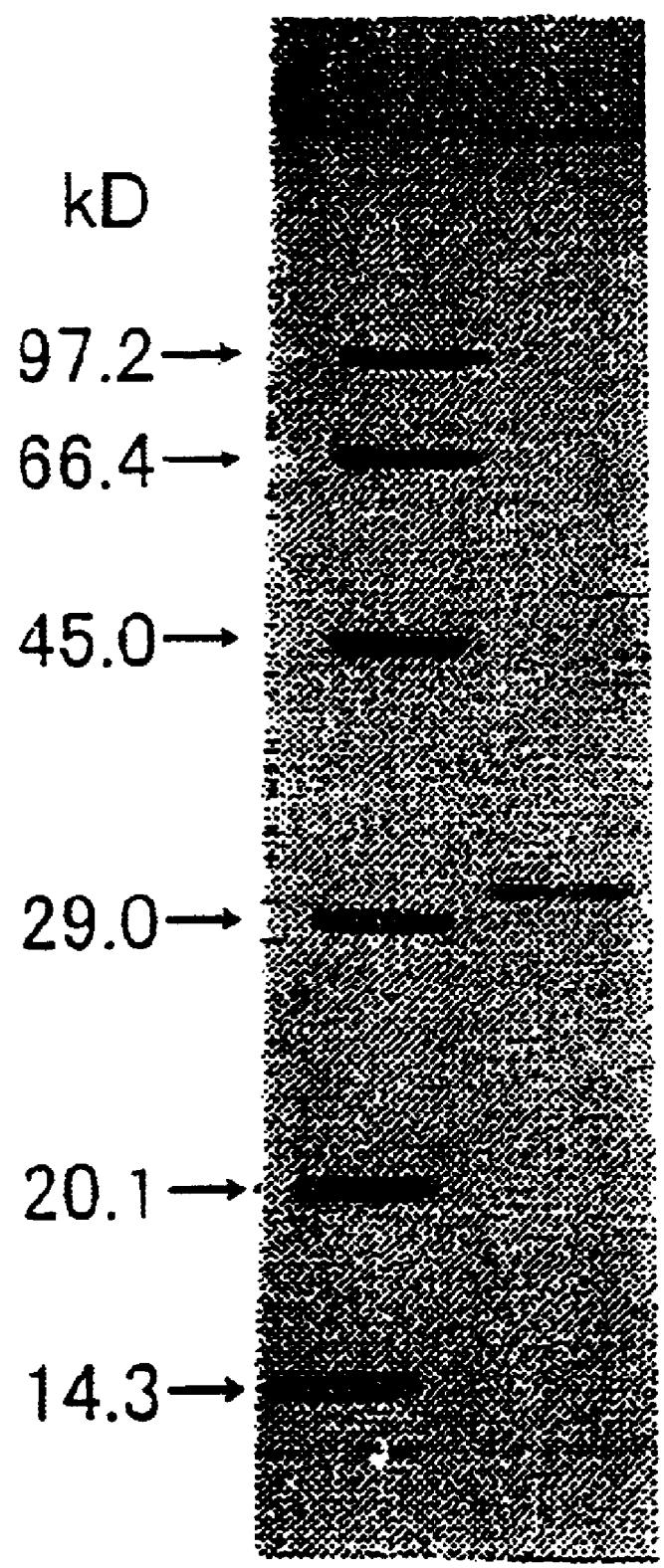
FIG. 1 shows the sodium dodecylsulfate polyacrylamide gel electrophoresis (SDS-PAGE) pattern.

The carbonyl reductase of this invention characteristically uses NADH as a coenzyme and reduces 4-chloroacetoacetate ester but does not substantially dehydrogenate any optical isomers of 4-halo-3-hydroxybutyrate ester.

In the present invention, the 4-chloroacetoacetate ester-reducing activity of the enzyme can be identified as follows.
Method of Assaying the 4-Chloroacetoacetate Ester-Reducing Activity of the Enzyme A decrease of absorbance at 340 nm, following a decrease of NADH, is measured during the reaction at 30 in a reaction mixture containing 50 mM potassium phosphate buffer (pH 6.5), 0.2 mM NADH, 20 mM ethyl 4-chloroacetoacetate, and the enzyme. One unit of the enzyme of the present invention is defined as the amount required to decrease 1 mole of NADH in 1 min. A protein is quantitated by the dye-binding method using a Protein Assay Kit (BioRad).

When NADH cannot be used as a coenzyme, a decrease of absorbance at 340 nm can be only slightly observed under the conditions described above. The carbonyl reductase of the present invention shows higher activity in the presence of NADH as an electron donor instead of NADPH. Namely, NADH has significantly higher activity for the enzyme as an electron donor than NADPH. The electron donor more suitable as a coenzyme can be clearly shown by assaying the activities of the enzyme in the presence of either NADPH or NADH under the above reaction conditions and comparing the results.

The carbonyl reductase of this invention has high 4-chloroacetoacetate ester-reducing activity but does not substantially dehydrogenate (i.e., oxidize) any optical isomers of 4-halo-3-hydroxybutyrate ester. That the enzyme does not substantially dehydrogenate 4-halo-3-hydroxybutyrate ester can be judged as follows. The enzyme contacts the substrate, 4-halo-3-hydroxybutyrate ester, in the presence of $NAD^+$, and the change (per unit time) of the absorbance at 340 nm, which is accompanied with an increase or decrease of NADH, is measured. When the change rate is 5% or less, preferably 1% or less, taking the change of the absorbance at 340 nm where 4-chloroacetoacetate ester is used as 100%, the enzyme does not have substantial dehydrogenase activity.

In a preferred embodiment of the present invention, the carbonyl reductase does not substantially dehydrogenate isopropanol and does not reduce acetoacetate ester. That the enzyme does not have the above activities can also be judged, as described above, when the change rates of absorbance at 340 nm measured using the above substrates are 5% or less, preferably 1% or less, taking the rate where 4-chloroacetoacetate ester is used as a substrate as 100%.

The carbonyl reductase having the physicochemical properties described above is purified from, for example, cultured cells of yeast Kluyveromyces. In particular, Kluyveromyces aestuarii is preferably used in the present invention since it produces the carbonyl reductase of the present invention in a high yield. The strains of Kluyveromyces aestuarii, for example, Kluyveromyces aestuarii IFO 10597 and IFO 10598, that produce the carbonyl reductase of this invention, are available from the Institute for Fermentation, Osaka (IFO) and recited in List of Cultures 10th ed. (1996) published by IFO.

The above microorganisms are cultivated in a medium usually used for fungi such as YM medium. After sufficient cultivation, grown cells are collected and disrupted in a buffer containing a reducing agent such as 2-mercaptoethanol and a protease inhibitor such as phenyl-methanesulfonyl fluoride (PMFS) to obtain cell-free extracts. The enzyme can be purified from the thus-obtained cell-free extracts by a protein solubility-dependent fractionation (precipitation by organic solvent, salting out by ammonium sulfate, etc.), and an appropriate combination of chromatography such as cation or anion exchange chromatography, gel filtration, hydrophobic chromatography, and affinity chromatography using chelate, dye, antibody, etc. The enzyme can be purified by, for example, hydrophobic chromatography using phenyl-Toyopearl, anion exchange chromatography using Q-sepharose, butyl-Toyopearl hydrophobic chromatography, affinity chromatography using blue sepharose, gel filtration using Superdex 200, etc. After these purification procedures, the enzyme can be electrophoretically purified to almost a single band.

In the present invention, the carbonyl reductase derived from Kluyveromyces aestuarii is a polypeptide having the following physicochemical properties:

(1) Reactivity

It reduces 4-haloacetoacetate ester to produce (S)-4-halo-3-hydroxybutyrate ester using reduced beta-nicotinamide adenine dinucleotide as an electron donor;

(2) Substrate Specificity

It has high reductase activity to 4-chloroacetoacetate ester but does not substantially dehydrogenate any optical isomers of 4-halo-3-hydroxybutyrate ester and shows higher enzymatic activity when used with reduced beta-nicotinamide adenine dinucleotide as an electron donor than reduced beta-nicotinamide adenine dinucleotide phosphate.

In addition, the enzyme can have the physicochemical properties below.

(3) Optimal pH 5.0 to 6.0

(4) Substrate Specificity

The enzyme does not substantially dehydrogenate isopropanol and does not reduce acetoacetate ester.

(5) Molecular Weight

The molecular weight of the enzyme is 32,000 using sodium dodecylsulfate polyacrylamide gel electrophoresis (SDS-PAGE).

Furthermore, this enzyme can have properties described below.

(6) pH Stability relatively stable in the range of pH 7 to 11

(7) Optimal Temperature 40 to 45

(8) Thermostability relatively stable up to 40

(9) Inhibition

This enzyme is inhibited by SH reagents such as p-chloromercuribenzoic acid (PCMB) and copper sulfate. The enzyme is weakly inhibited by iodoacetamide but is not inhibited by quercetin or barbital.

This invention relates to an isolated nucleic acid encoding a carbonyl reductase and homologues of the enzyme. An "isolated nucleic acid" is a nucleic acid which has a non-naturally occurring sequence, or which has the sequence of part or all of a naturally occurring gene but is free of the genes that flank the naturally occurring gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Specifically excluded from this definition are mixtures of DNA molecules, vectors, or clones as they occur in a DNA library such as a cDNA or genomic DNA library. Also excluded are RNA molecules that consist of naturally-occurring sequences (e.g., naturally-occurring mRNA), except where the RNA is in a purified state such that it is at least 90% free of other naturally-occurring RNA species. Thus, a naturally-occurring mRNA in a whole mRNA preparation prepared from a cell would not be an "isolated nucleic acid," but a single mRNA species purified to 90% homogeneity from that whole mRNA preparation would be.

The nucleic acid encoding the carbonyl reductase of this invention comprises, for example, the nucleotide sequence represented by SEQ ID NO: 1. The nucleotide sequence represented by SEQ ID NO: 1 encodes a polypeptide consisting of the amino acid sequence represented by SEQ ID NO: 2. Nucleic acid homologues encoding the carbonyl reductase of the present invention comprise the amino acid sequence represented by SEQ ID NO: 2 in which one or more amino acids are deleted, substituted, inserted, and/or added, and DNAs encoding the polypeptide having physicochemical properties described in (1) and (2). It will be apparent to those skilled in the art that modifications such as substitution, deletion, insertion, and/or addition may be made in the DNA described in SEQ ID NO: 1 using site-directed mutagenesis (Nucleic Acid Res. 10, pp. 6487 (1982), Methods in Enzymol. 100, pp. 448 (1983), Molecular Cloning 2nd Ed., Cold Spring Harbor Laboratory Press (1989), PCR A Practical Approach IRL Press pp. 200 (1991)), and the like, to obtain homologues.

The nucleic acid homologues of the present invention hybridize with a DNA consisting of the nucleotide sequence represented by SEQ ID NO: 1 under stringent conditions, and encode a polypeptide having physicochemical properties (1) and (2) described above. DNAs that hybridize under stringent conditions are defined to be DNAs hybridizing with one or more DNA probes such as any DNA fragments sequentially containing at least 20 bases, preferably at least 30 bases, for example, 40 bases, 60 bases, or 100 bases of the DNA sequence represented by SEQ ID NO: 1 under the hybridization conditions: 37° C., 1×SSC; followed by washing at 42° C., 0.5×SSC.

The nucleic acid homologues of the present invention comprise a nucleic acid encoding a polypeptide having at least 70%, preferably at least 80% or 90%, and more preferably 95% or more homology with the amino acid sequence represented by SEQ ID NO: 2.

To determine the "percent homology (identity)" of two nucleic acids or of two amino acids, the sequences are aligned for optimal comparison purposes (e.g., gaps can be introduced in the sequence of a first nucleic acid or amino acid sequence for optimal alignment with a second nucleic acid or amino acid sequence). The nucleotides or amino acid residues at corresponding nucleotide positions or amino acid positions are then compared. When a position in the first sequence is occupied by the same nucleotide or amino acid residue as the corresponding position in the second sequence, then the molecules are identical at that position. The percent homology between the two sequences is a function of the number of identical positions shared by the sequences (i.e., % identity=# of identical positions/total # of positions (e.g., overlapping positions×100). In one embodiment the two sequences are the same length.

Based on the above general principles, the "percent identity" of two amino acid sequences or of two nucleic acids is determined using the algorithm of Karlin and Altschul (Proc. Natl. Acad. Sci. USA 87:2264–2268, 1990), modified as in Karlin and Altschul (Proc. Natl. Acad. Sci. USA 90:5873–5877, 1993). Such an algorithm is incorporated into the NBLAST and XBLAST programs of Altschul et al. (J. Mol. Biol. 215:403–410, 1990). BLAST nucleotide searches are performed with the NBLAST program, score= 100, wordlength=12. BLAST searches are performed with the XBLAST program, score=50, wordlength=3. Where gaps exist between two sequences, Gapped BLAST is utilized as described in Altschul et al. (Nucleic Acids Res. 25:3389–3402, 1997). When utilizing BLAST and Gapped BLAST programs, the default parameters of the respective programs (e.g., XBLAST and NBLAST) are used. See http://www.ncbi.nlm.nih.gov.

The carbonyl reductase of the present invention includes a substantially pure polypeptide comprising the amino acid sequence described in SEQ ID NO: 2 and having the physicochemical properties (1) and (2) above, and its homologues. The term "substantially pure" used herein in reference to a given polypeptide means that the polypeptide is substantially free from other biological compounds, such as those in cellular material, viral material, or culture medium, with which the polypeptide may have been associated (e.g., in the course of production by recombinant DNA techniques or before purification from a natural biological source). The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

A preferable example of the polypeptide of the present invention is a polypeptide comprising the amino acid sequence described in SEQ ID NO: 2.

Homologues of the carbonyl reductase of the present invention include the amino acid sequence described in SEQ ID NO: 2 in which one or more amino acids are deleted, substituted, inserted, and/or added. It will be apparent to those skilled in the art that such modifications as substitution, deletion, insertion, and/or addition may be made in the DNA described in SEQ ID NO: 1 using site-directed mutagenesis (Nucleic Acid Res. 10, pp. 6487 (1982), Methods in Enzymol. 100, pp. 448 (1983), Molecular Cloning 2nd Ed., Cold Spring Harbor Laboratory Press (1989), PCR A Practical Approach IRL Press pp. 200 (1991)), etc., thereby obtaining DNAs encoding homologues of the carbonyl reductase. The DNA encoding a homologue of the carbonyl reductase is introduced into host cells and expressed to obtain the homologue of the carbonyl reductase described in SEQ ID NO: 2.

The homologues of the carbonyl reductase of the invention can also be a substantially pure polypeptide comprising the amino acid sequence represented by SEQ ID NO: 2 containing up to 30 conservative amino acid substitutions, and having the physicochemical properties (1) and (2).

A "conservative amino acid substitution" is one in which the amino acid residue is replaced with another residue having a chemically similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

More specifically, homologues of the carbonyl reductase of the present invention are polypeptides having at least 70%, preferably at least 80% or 90%, and more preferably 95% or more homology with the amino acid sequence represented by SEQ ID NO: 2. The percent homology between the two amino acid sequences can be determined as described above. A homology search of the amino acid sequence described in SEQ ID NO: 2 was actually performed by using the BLAST program in DDBJ. As a result, Sorbitol Utilization Protein SOU1 derived from *Candida albicans* was found to have the highest homology (63%) among known proteins.

An nucleic acid encoding the carbonyl reductase of the present invention can be isolated by, for example, the method described below.

The N-terminal amino acid sequence of the purified enzyme of the present invention is determined. The enzyme is cleaved with lysyl endopeptidase, V8 protease, etc., and the peptide fragments are purified by reversed-phase liquid chromatography, etc. The amino acid sequence of the peptide fragments thus obtained can be determined by a protein sequencer.

A fragment of the nucleic acid of the present invention can be obtained in the following manner. The primers for PCR are designed based on the amino acid sequence determined. A portion of the nucleic acid of the present invention can then be amplified by PCR using the designed primers and chromosomal DNAs or cDNA libraries of cells that produce the enzyme as a template.

Furthermore, the thus-obtained nucleic acid fragments can be used to obtain the nucleic of this invention as follows. Libraries and cDNA libraries are prepared from *E. coli* transformed with a phage, plasmid, etc. into which a restriction endonuclease-digest of a chromosomal DNA from enzyme-producing strains is inserted. The thus-obtained libraries and cDNA libraries can then be used for colony hybridization and plaque hybridization using the amplified DNA as a probe, thereby obtaining the nucleic acid of this invention.

The nucleic acid of the present invention can also be obtained in the following manner. Primers for PCR are designed to extend a known DNA fragment based on the sequence obtained by analyzing the nucleotide sequences of the amplified DNA fragments. Chromosomal DNAs from the enzyme-producing strains are digested with appropriate restriction endonucleases. An inverse PCR (Genetics 120, 621–623 (1988)) is then performed using the self-circularized DNA formed from the above digests as a template and the primers. The RACE (Rapid Amplification of cDNA End, "PCR Experiment Manual" p 25–33, HBJ Academic Press) method, etc. can also be used, thereby obtaining the nucleic acid of this invention.

Thus, the nucleic acid of the present invention can be obtained by cloning genome DNA and cDNA using the above methods. Alternatively, the nucleic acid of the invention can be synthesized.

A vector expressing the enzyme of the present invention can be provided by inserting the thus-obtained nucleic acid encoding the carbonyl reductase of the invention into a known expression vector. The carbonyl reductase of the present invention can be produced by cultivating a transformant harboring this expression vector.

In the present invention, microorganisms to be transformed for expression of the carbonyl reductase requiring NADH as an electron donor are not limited as long as they can be transformed with the recombinant vector containing the nucleic acid encoding the polypeptide having the carbonyl reductase activity requiring NADH as an electron donor and can express the polypeptide. Examples of the microorganisms include those for which host-vector systems are developed, such as bacteria belonging to the genus *Escherichia, Bacillus, Pseudomonas, Serratia, Brevibacterium, Corynebacterium, Streptococcus,* or *Lactobacillus*; actinomycetes belonging to the genus *Rhodococcusor* or *Streptomyces*; yeast belonging to the genus *Saccharomyces, Kluyveromyces, Schizosaccharomyces, Zygosaccharomyces, Yarrowia, Trichosporon, Rhodosporidium, Hansenula, Pichia,* or *Candida*; fungi belonging to the genus *Neurospora, Aspergillus, Cephalosporium,* or *Trichoderma*.

The procedure for generating transformants and constructing recombinant vectors suitable for hosts can be performed according to standard techniques known in the fields of molecular biology, bioengineering, and genetic engineering (for example, Sambrook et al., Molecular Cloning, Cold Spring Harbor Laboratories). The transformants such as microorganisms stably maintaining DNA-inserted phages or plasmids should transcript and translate the genetic information so as to express the carbonyl reductase gene of the present invention requiring NADH as an electron donor. An IA promoter that regulates transcription and translation is inserted 5'-upstream of the DNA of the present invention; preferably, a terminator is also inserted 3'-downstream of the DNA. The promoter and terminator should function in microorganisms to be used as host cells. Vectors, promoters, and terminators functioning in various microorganisms are described in "Biseibutsugaku Kisokouza (Basic Course of Microbiology) Vol. 8 Idenshikougaku (Genetic Engineering), Kyoritsu Shuppan Co., Ltd., particularly for yeast, described in "Adv. Biochem. Eng. 43, 75–102 (1990), Yeast 8, 423–488 (1992)" etc.

For example, plasmid vectors such as pBR and pUC series, and promoters such as those of -galactosidase (lac), tryptophan operon (trp), tac, trc (fusion of lac and trp), and those derived from -phage PL, PR, etc. can be used for the genus Escherichia, particularly *Escherichia coli*. Terminators derived from trpA, phage, and rrn ribosomal RNA can also be used.

Vectors such as the pUB110 and pC194 series can be used for the genus *Bacillus* and can be integrated into chromosomes. Promoters and terminators such as those of alkaline protease (apr), neutral protease (npr), and -amylase (amy) can be used.

Host-vector systems for the genus *Pseudomonas*, specifically *Pseudomonas putida* and *Pseudomonas cepacia*, have been developed. A broad host range vector pKT240 (containing genes necessary for autonomous replication derived from RSF1010) based on plasmid TOL that is involved in degradation of toluene compounds can be utilized. A promoter and terminator of a lipase (JP-A Hei 5-284973) gene and the like can be used.

Plasmid vectors such as pAJ43 (Gene 39, 281 (1985)) can be used for the genus *Brevibacterium*, especially *Brevibacterium lactofermentum*. Promoters and terminators for the genus *Escherichia* can be used for this microorganism.

Plasmid vectors such as pCS11 (JP-A Sho 57-183799) and pCB101 (Mol. Gen. Genet. 196, 175 (1984)) can be used for the genus *Corynebacterium*, particularly, *Corynebacterium glutamicum*.

Plasmid vectors such as pHV1301 (FEMS Microbiol. Lett., 26, 239 (1985)) and pGK1 (Appl. Environ. Microbiol. 50, 94 (1985)) can be used for the genus *Streptococcus*.

For the genus *Lactobacillus*, pAM 1 developed for the genus *Streptococcus* (J. Bacteriol. 137, 614 (1979)) can be used, and some of the promoters for the genus *Escherichia* are applicable.

For the genus *Rhodococcus*, a plasmid vector isolated from *Rhodococcus rhodochrous* can be used (J. Gen. Microbiol. 138, 1003 (1992)).

Plasmids functioning in the genus *Streptomyces* can be constructed by the method described in "Genetic Manipulation of Streptomyces: A Laboratory Manual Cold Spring Harbor Laboratories by Hopwood et al. (1985)." For example, pIJ486 (Mol. Gen. Genet. 203, 468–478 (1986)), pKC1064 (Gene 103, 97–99 (1991)), and pUWL-KS (Gene 165, 149–150 (1995)) can be used, particularly for *Streptomyces lividans*. Such plasmids can also be used for *Streptomyces virginiae* (Actinomycetol. 11, 46–53 (1997)).

Plasmids such as the YRp, YEp, YCp, and YIp series can be used for the genus *Saccharomyces*, especially for *Saccharomyces cerevisiae*. Integration vectors (such as EP 537456) using homologous recombination with multiple copies of a ribosomal DNA in genomic DNA are extremely useful because they are capable of introducing multiple copies of genes into the host genome and stably maintaining the genes. Furthermore, promoters and terminators of alcohol dehydrogenase (ADH), glyceraldehyde-3-phosphate dehydrogenase (GAPDH), acid phosphatase (PHO), -galactosidase (GAL), phosphoglycerate kinase (PGK), enolase (ENO), etc. can be used.

Plasmids such as the series of 2 m plasmids derived from *Saccharomyces cerevisiae*, the series of pKD1 plasmids (J. Bacteriol. 145, 382–390 (1981)), plasmids derived from pGK11 involved in killer activity, the series of KARS plasmids containing an autonomous replication gene from the genus *Kluyveromyces*, and vector plasmids (such as EP 537456) capable of being integrated into chromosomes by homologous recombination with ribosomal DNA can be used for the genus *Kluyveromyces*, particularly for *Kluyveromyces lactis*. Promoters and terminators derived from ADH and PGK are applicable.

For the genus *Schizosaccharomyces*, plasmid vectors containing ARS (a gene involved in autonomous replication) derived from *Schizosaccharomyces pombe* and containing selective markers supplementing auxotrophy of *Saccharomyces cerevisiae* can be used (Mol. Cell. Biol. 6, 80 (1986)). Furthermore, ADH promoter derived from *Schizosaccharomyces pombe* is applicable (EMBO J. 6, 729 (1987)). In particular, pAUR224 is commercially available from Takara Shuzo.

For the genus *Zygosaccharomyces*, plasmid vectors such as pSB3 (Nucleic Acids Res. 13, 4267 (1985)) derived from *Zygosaccharomyces rouxii* can be used. Promoters of PHO5 derived from *Saccharomyces cerevisiae* and glycerolaldehyde-3-phosphate dehydrogenase (GAP-Zr) derived from *Zygosaccharomyces rouxii* (Agri. Biol. Chem. 54, 2521 (1990)), etc. are available.

For the genus *Hansenula*, host-vector systems have been developed for *Hansenula polymorpha*. Genes (HARS1, HARS2) involved in autonomous replication derived from *Hansenula polymorpha* can be used as vectors. These genes cannot be maintained stably, so multiple copies of them should be integrated into chromosomes (Yeast 7, 431–443 (1991)). Promoters of alcohol oxidase (AOX) that is induced by methanol and the like and formic acid dehydrogenase (FDH) can be used.

For the genus *Pichia*, host-vector systems for *Pichia pastoris* have been developed using genes such as PARS1 and PARS2 involved in autonomous replication derived from *Pichia* (Mol. Cell. Biol. 5, 3376 (1985)). Promoters such as a promoter of AOX with strong promoter activity induced by high-density culture and methanol are applicable (Nucleic Acids Res. 15, 3859 (1987)).

For the genus *Candida*, host-vector systems have been developed for *Candida maltosa, Candida albicans, Candida tropicalis, Candida utilis*, etc. Vectors for *Candida maltosa* using ARS, which was cloned from this strain, have been developed (Agri. Biol. Chem. 51, 51, 1587 (1987). Strong promoters for vectors that are able to be integrated into chromosomes have been developed for *Candida utilis* (JP-A Hei 08-173170).

In the genus *Aspergillus, Aspergillus niger* and *Aspergillus oryzae* have been most extensively studied. Plasmids able to be integrated into chromosomes are available. Promoters derived from extracellular protease and amylase are available (Trends in Biotechnology 7, 283–287 (1989)).

For the genus *Trichoderma*, host-vector systems based on *Trichoderma reesei* have been developed, and promoters derived from extracellular cellulase genes are available (Biotechnology 7, 596–603 (1989)).

Various host-vector systems for plants and animals, in addition to microorganisms, have been developed. In particular, expression systems for producing a large amount of foreign proteins in insects, particularly silkworms (Nature 315, 592–594 (1985)), and plants such as rape seeds, corns, and potatoes have been developed and are available.

In the present invention, microorganisms capable of producing the enzyme that reduces 4-haloacetoacetate ester include all strains belonging to the genus *Kluyveromyces*, their mutants and variants capable of producing the NADH-dependent carbonyl reductase, and genetically engineered transformants that have acquired the capacity of producing the enzyme.

The present invention relates to the production of alcohol by reducing ketone using the above carbonyl reductase. The carbonyl reductase of this invention is industrially advantageous since it can use NADH as a coenzyme, which is less expensive and more stable than NADPH. The desired enzymatic reaction can be performed by contacting the reaction solution with the enzyme molecules, their treated products, cultured broth containing the enzyme molecules, or living transformants such as microorganisms producing the enzymes. Furthermore, the contact of the reaction solution with the enzyme is not limited thereto. The reaction solution is defined as an appropriate solvent containing a substrate and NADH that is a coenzyme necessary for the enzymatic reaction, wherein the solvent provides circumstances desirable for the enzyme to express the enzyme activity. The treated microorganisms containing the carbonyl reductase of the present invention include microorganisms whose cell membrane permeability is modified by treating them with surfactants or organic solvents such as toluene, cell-free extracts obtained by disrupting the microorganisms with glass beads, or by treating them with enzyme, the partially purified preparation of the extracts, etc. The microbial cells can also be used by being immobilized on carageenan gel, alginate gel, polyacrylamide gel, cellulose, agar, or the like supporting material, using a known method.

The ketone used in the method for producing alcohol according to the present invention, 2,3-butandione, with neighboring diketones and 4-haloacetoacetate ester derivatives is preferable. Halogen atoms of ethyl 4-haloacetoacetate derivatives include bromine, iodine, and chlorine, but preferably chlorine. Examples of esters include those of alcohol having linear chains, branched chains, and aromatic substitutions, such as methyl, ethyl, propyl, isopropyl, butyl, octyl, and benzyl esters. Ethyl ester is most preferable. The 4-haloacetoacetate ester derivatives include, for example, those with alkyl groups containing a linear chain or branched chain at the 2-position and halogens such as chlorine, bromine, and iodine.

$NAD^+$ formed from NADH during reductive reactions can be converted into NADH using the $NAD^+$-reduction ability of microorganisms (glycolytic pathway, catabolic pathway of C1 compounds in methylotroph). The ability of the $NAD^+$-reduction can be enhanced by adding glucose, ethanol, formic acid, etc. to a reaction system. Furthermore, the above enhancement can be achieved by adding microorganisms, their treated products, or their enzymes capable of forming NADH from $NAD^+$ to the reaction system. For example, microorganisms having glucose dehydrogenase, formate dehydrogenase, alcohol dehydrogenase, amino acid dehydrogenase, or organic acid dehydrogenase (malate dehydrogenase and so on); their treated products; their enzymes that are partially or highly purified can be used. The reactants necessary for regenerating NADH can be added to the reaction system for producing alcohol of the present invention as they are, in immobilized forms, or through a membrane capable of regenerating NADH.

Such additional reaction systems for regenerating NADH are unnecessary when living transformants containing a recombinant vector harboring the DNA of this invention are used in the above-described method for producing alcohol. Namely, NADH is efficiently regenerated without adding the enzyme for NADH regeneration in the reduction reaction with transformant microorganisms if the microorganisms have high NADH regenerating activity. It is also possible to express the NADH-regenerating enzyme and NADH-dependent carbonyl reductase and to perform the reduction reaction using them more efficiently by introducing a gene encoding the NADH-regenerating enzyme such as glucose dehydrogenase, formate dehydrogenase, alcohol dehydrogenase, amino acid dehydrogenase, or organic acid dehydrogenase (malate dehydrogenase and so on) to a host cell together with the DNA encoding the NADH-dependent carbonyl reductase of this invention. These two or more genes can be introduced into a host by transforming a host with recombinant vectors each having different replication origin and each enzyme gene to avoid incompatibility, transforming a host with a single vector into which the genes are inserted, or introducing the genes into host chromosomes. When two or more genes are introduced into a single vector, each gene is ligated with gene expression-regulating regions including promoters and terminators. Alternatively, the genes are expressed as an operon containing two or more cistrons such as a lactose operon.

The reduction reaction using the enzyme of the present invention can be performed in water; a water-insoluble organic solvent such as ethyl acetate, butyl acetate, toluene, chloroform, or n-hexane; or a two-phase system of such a solvent and an aqueous solvent.

The reaction of this invention can be performed using an immobilized enzyme, a membrane reactor, etc.

The reaction of this invention can be performed at temperatures ranging from 4 to 60, preferably 10 to 37; a pH ranging from 3 to 11; preferably 5 to 8; and the concentration of substrates ranging from 0.01 to 90 w/v %, preferably 0.1 to 30 w/v % based on the reaction mixture. $NAD^+$ or NADH can be added to the reaction system as a coenzyme in a concentration ranging from 0.001 to 100 mM, preferably 0.01 to 10 mM. The substrate can be added once at the beginning of the reaction. Preferably, it is added continuously or several times with divided portions to prevent the concentration of the substrate from becoming too high in the reaction system.

Compounds added to the reaction system for regenerating NADH, for example, glucose in case of using glucose dehydrogenase, formic acid in case of using formate dehydrogenase, and ethyl alcohol or isopropanol in case of using alcohol dehydrogenase, can be added at a molar ratio of 0.1 to 20, and preferably 1 to 5 or more per mole of the substrate, ketone. The enzymes for regenerating NADH, for example, glucose dehydrogenase, formate dehydrogenase, and alcohol dehydrogenase, can be added in an amount of 0.1- to 100-fold, and preferably 0.5- to 20-fold, enzymatic activity based on that of the NADH-dependent carbonyl reductase of this invention.

Alcohol formed by the reduction reaction of ketone according to the present invention can be purified from the cells and proteins by appropriate combinations of known purification techniques such as centrifugation, membrane treatment, solvent extraction, or distillation.

For example, the cells are removed from the reaction solution by centrifugation, proteins are removed by ultrafiltration, and solvents such as ethyl acetate and toluene are added to the filtrate to extract 4-halo-3-hydroxyacetate ester into the solvent layer. The organic solvent layer is subjected to phase separation and distilled to obtain 4-halo-3-hydroxyacetate ester with high purity.

The NADH-dependent carbonyl reductase and the DNA encoding the enzyme of the present invention are advantageous in the industrial production of alcohols. The method of the present invention using the above enzyme enables efficiently producing (S)-4-halo-3-hydoxybutyrate ester with high optical purity.

The following examples further illustrate this invention but are not to be construed to limit the scope of the invention.

EXAMPLE 1

Purification of Carbonyl Reductase

*Kluyveromyces aestuarii* IFO 10597 was cultured in 20 L of YM medium containing 24 g/L glucose, 3 g/L yeast extract, 3 g/L malt extract, and 5 g/L peptone (pH 6.0). The cultured cells were harvested by centrifugation. The wet cells thus obtained were suspended in 50 mM potassium phosphate buffer (pH 8.0) containing 0.02% 2-mercaptoethanol and 2 mM phenylmethanesulfonyl fluoride (PMSF). The suspended cells were disrupted with a bead beater (BioSpec Co.), then cell debris was removed by centrifugation to obtain cell-free extracts. After protamine sulfate was added to the thus-obtained cell-free extract, the mixture was centrifuged to obtain a nucleic acid-free supernatant. The supernatant was adjusted to 25% saturation with ammonium sulfate and was applied to a phenyl-Toyopearl 650M column (5.0 cm×27 cm) equilibrated with a standard buffer (10 mM potassium phosphate buffer (pH 8.0), 0.01% 2-mercaptoehanol) containing 25% ammonium sulfate. Elution was then performed with a linear gradient of ammonium sulfate solution from a concentration of 25 to 0%.

The activity of the carbonyl reductase was detected in three fractions, a passed-through fraction and two gradient-eluted fractions. The latest fraction among the three fractions was pooled and concentrated by ultrafiltration.

After the concentrated enzyme solution was dialyzed against a standard buffer, the dialysate was applied to a Q-sepharose HP column (2.6 cm×10 cm) equilibrated with the standard buffer. The column was subsequently washed with the standard buffer and the standard buffer containing 0.2 M NaCl. Elution was performed with a linear gradient of NaCl solution from 0.2 to 0.9 M. Active eluted fractions were pooled and concentrated by ultrafiltration.

The concentrated enzyme solution was adjusted to 20% saturation with ammonium sulfate and was applied to a butyl-Toyopearl 650M column (1.6 cm×5 cm) equilibrated with the standard buffer containing 20% saturation ammonium sulfate. The column was washed with the same buffer, and elution was performed with a linear gradient of ammonium sulfate solution from a concentration of 20 to 0%. The peak of the activity of the carbonyl reductase was detected in two eluted fractions. The first fraction with major activity was pooled.

After the concentrated active fraction was dialyzed against the standard buffer, the enzyme solution was loaded on a Blue-sepharose HP column (1.6 cm×2.5 cm) equilibrated with the same buffer, and the column was then washed with the standard buffer. Elution was performed with a linear gradient of NaCl solution from 0 to 1 M. The passed-through fraction in which the activity of the carbonyl reductase was detected was pooled and concentrated. The concentrated enzyme solution was subjected to gel filtration with Superdex 200 column (1.6 cm×100 cm using the standard buffer containing 0.3 M NaCl).

The active fractions obtained by gel filtration were concentrated and analyzed by polyacrylamide gel electrophoresis (PAGE). The enzyme was detected as a substantially single band (FIG. 1).

The specific activity of the purified enzyme was about 28.6 U/mg. The purification steps of the enzyme are shown in Table 1.

TABLE 1

| Purification step | Protein (mg) | Enzyme activity (U) | Specific activity (U/mg) |
|---|---|---|---|
| Cell-free extract | 55700 | 3610 | 0.0648 |
| Protamin sulfate precipitation | 28500 | 4730 | 0.166 |
| Phenyl-Toyopearl | 591 | 83.2 | 0.141 |
| Q-Sepharose | 50.0 | 42.8 | 0.856 |
| Butyl-Toyopearl | 3.62 | 23.6 | 6.52 |
| Blue-sepharose | 0.21 | 3.00 | 14.3 |
| Superdex 200 | 0.021 | 0.60 | 28.6 |

EXAMPLE 2

Molecular Weight of Carbonyl Reductase

The molecular weight of the subunit of the enzyme obtained in Example 1 was determined to be 32 kDa by SDS-PAGE. The molecular weight determined by gel filtration using Superdex G200 was approximately 85 kDa.

EXAMPLE 3

Optimal pH of the Carbonyl Reductase

Figure 2:
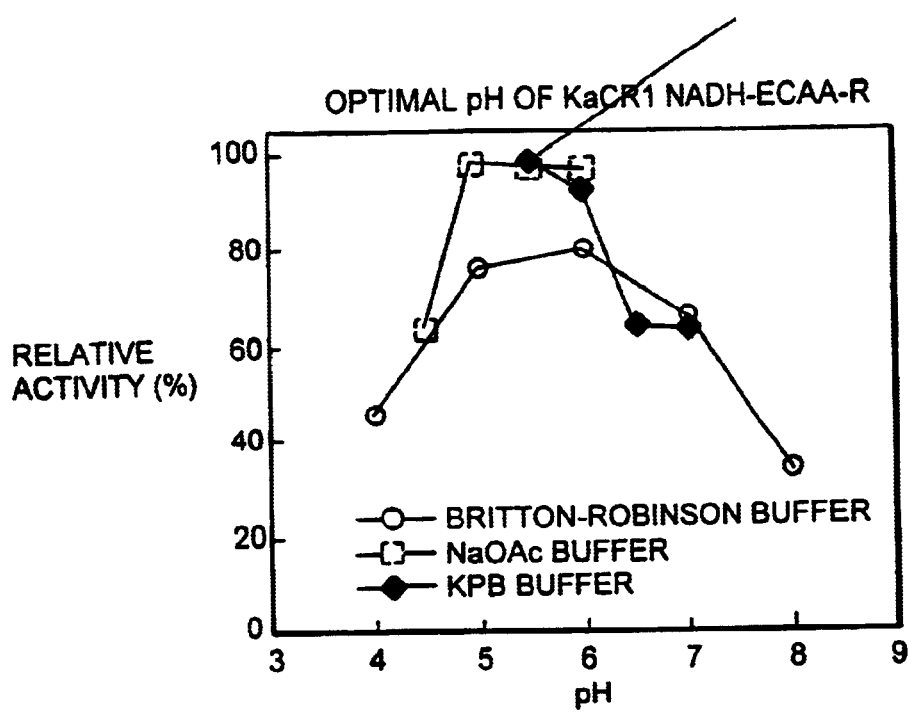
FIG. 2 shows the pH-dependence of the ethyl 4-chloroacetoacetate-reducing activity of the carbonyl reductase produced in Example 1. In the figure, circles represent results using Britton-Robinson buffer; squares, sodium acetate buffer; and triangles, potassium phosphate buffer.

The relative reductase activity of the enzyme obtained in Example 1 to ethyl 4-chloroacetoacetate was investigated with varying pH values of the reaction solution using the potassium phosphate buffer, the sodium acetate buffer, and the Britton-Robinson buffer. The results are shown in FIG. 2 as activity relative to the maximum activity that is regarded as 100. The optimal pH of the reaction was estimated to be pH 5.0 to 6.0.

EXAMPLE 4

Optimal Temperature of the Carbonyl Reductase

Figure 3:
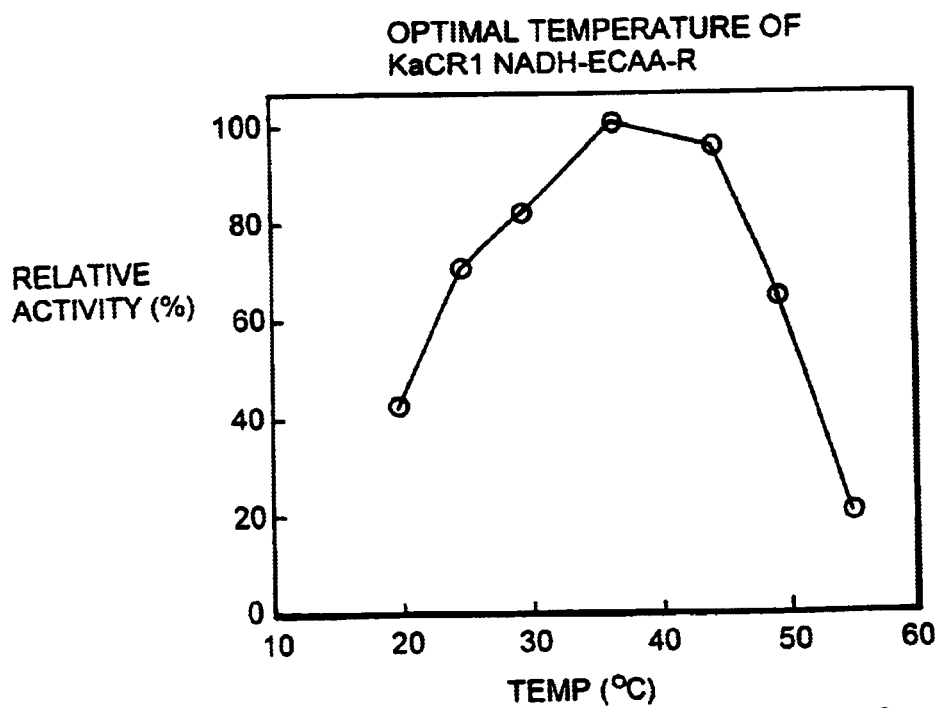
FIG. 3 shows the temperature-dependence of the ethyl 4-chloroacetoacetate-reducing activity of the carbonyl reductase produced in Example 1.

The reductase activity of the enzyme obtained in Example 1 with respect to ethyl 4-chloroacetoacetate was determined under the standard reaction condition with varying reaction temperatures. The results are shown in FIG. 3 as the activity relative to the maximum activity that is regarded as 100. The optimal temperature was determined to be 40 to 45.

EXAMPLE 5 pH Stability of the Carbonyl Reductase

Figure 4:
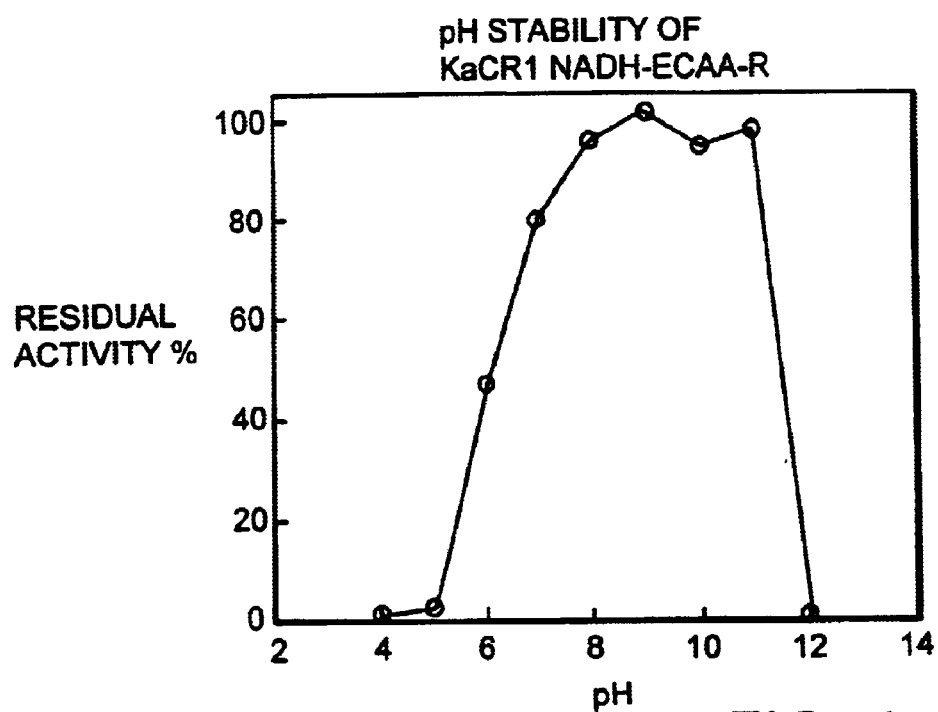
FIG. 4 shows the pH stability of the carbonyl reductase produced in Example 1.

The enzyme obtained in Example 1 was incubated at 30 for 30 min in the Briiton-Robinson buffer, ranging from pH 4 to 12, and the activities were measured. The results are shown in FIG. 4 as the residual activity to the activity of the untreated enzyme that is regarded as 100. The most stable pH of the carbonyl reductase of the present invention was determined to be pH 7.0 to 11.0.

EXAMPLE 6

Thermostability of the Carbonyl Reductase

Figure 5:
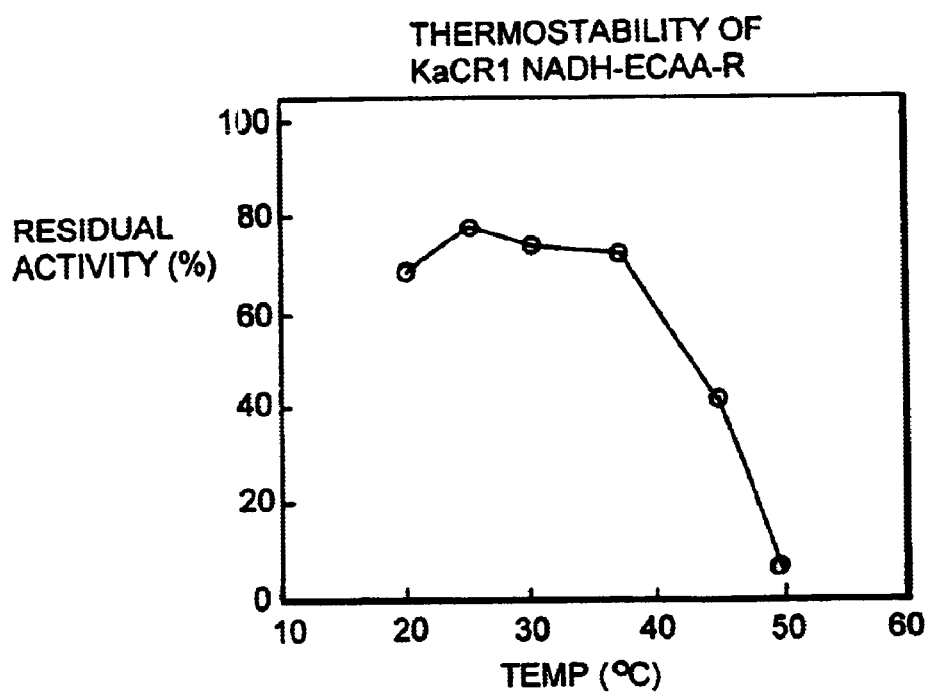
FIG. 5 shows the thermostability of the carbonyl reductase produced in Example 1.

The enzyme obtained in Example 1 was incubated at pH 8.0 for 10 min at 30, 37, 45, 50, and 55; the reductase activity of each incubation mixture to ethyl 4-chloroacetoacetate was then measured. The results are shown in FIG. 5 as the residual activity to the activity of the untreated enzyme that is taken as 100. The carbonyl reductase of the present invention showed 75% or more of the residual activity up to 37.

EXAMPLE 7

Substrate Specificity of the Carbonyl Reductase

The reductase activity of the enzyme obtained in Example 1 was measured by reacting the enzyme with various ketones and aldehydes in the presence of a coenzyme. The results are shown in Table 2 as the activity relative to that of ethyl 4-chloroacetoacetate in the presence of NADH that is taken as 100. The carbonyl reductase of the present invention showed only 6.4% of the activity in the presence of NADPH as a coenzyme to that in the presence of NADH that is taken as 100%. The enzyme showed that the relative activity to 2,3-butadione used as ketone was 70.6%. This enzyme did not show any $NAD^+$-dependent dehydroganase activity to ethyl(R) or (S)-4-chloro-3-hydroxybutyrate.

TABLE 2

| Substrate | Coenzyme | Relative activity (%) |
|---|---|---|
| Reduction reaction | | |
| ethyl 4-chloroacetoacetate | NADH | 100 |
|  | NADPH | 6.4 |
| methyl 4-chloroacetoacetate | NADH | 13.1 |
| ethyl acetoacetate | NADH | 0 |
| methyl acetoacetate | NADH | 0 |
| 2,3-butandione | NADH | 70.6 |
| 2,3-pentandione | NADH | 8.2 |
| 2,4-pentandione | NADH | 0 |
| Propionaldehyde | NADH | 2.5 |
| pyridin-3-aldehyde | NADH | 0 |
| Methylglyoxal | NADH | 0 |
| Acetophenone | NADH | 0 |
| Oxidation reaction | | |
| ethyl (R)-4-chloro-3-hydroxybutyrate | $NAD^+$ | 0 |
| ethyl (S)-4-chloro-3-hydroxybutyrate | $NAD^+$ | 0 |
| ethyl (R)-3-hydroxybutyrate | $NAD^+$ | 1.9 |
| ethyl (S)-3-hydroxybutyrate | $NAD^+$ | 0 |
| Isopropanol | $NAD^+$ | 0 |

EXAMPLE 8

Influence of the Carbonyl Reductase Inhibitors

The enzyme obtained in Example 1 was incubated at 30 for 10 min in the presence of various reagents, and its reductase activity to ethyl 4-chloro-3-hydroxybutyrate was measured. The results are shown in Table 3 as the residual activity to that obtained without any reagent that is taken as 100. The carbonyl reductase of this invention was significantly inhibited by p-chloromercuribenzoic acid and copper sulfate, but not by quercetin and barbital.

TABLE 3

| Inhibitor | Concentration | Residual activity |
|---|---|---|
|  |  | 100 |
| p-chloromercuribenzoic acid | 0.05 mM | 0 |
| iodoacetamide | 1 mM | 84.0 |
| copper sulfate | 1 mM | 19.0 |
| quercetin | 0.1 mM | 94.0 |
| barbital | 1 mM | 101 |
| Phenylmethanesulfonyl fluoride | 1 mM | 99.0 |

EXAMPLE 9

Synthesis of ethyl(S)-4-chloro-3-hydroxybutyrate by the Carbonyl Reductase [1]

The reaction was carried out at 30 overnight in a reaction mixture containing 100 mM potassium phosphate buffer (pH 6.5), 139.8 mg of NADH, 0.5 U of the carbonyl reductase, and 2% ethyl 4-chloro-3-hydoroxyacetoacetate. The optical purity of the formed ethyl 4-chloro-3-hydoroxybutyrate was measured as follows. Ethyl 4-chloro-3-hydoroxybutyrate was extracted from the reaction mixture with ethyl acetate. After the solvent was removed from the extract, the extract was subjected to a liquid chromatography using an optical resolution column, Chiralcel OD column (4.6 mm×25 cm, Daicel Chemical Industries, Co., Ltd.), using a mixture of n-hexane and isopropanol (9:2) as an eluent at a flow rate of 0.5 mL/min, monitored with RI. As a result, ethyl 4-chloro-3-hydroxybutyrate produced by the method of this invention was S-isomer with an optical purity of 99% ee or more.

The yield of ethyl 4-chloro-3-hydroxybutyrate formed from ethyl 4-chloro-3-hydroxyacetoacetate as the starting material was measured by gas chromatography. The gas chromatography was performed at 150 using a Thermon-3000 5% Chromosorb W 60–80 (AW-DMCS)(3.2 mm×210 cm, Shinwa Chemical Industries, Ltd.) and a hydrogen flame ionization detector (FID). The reaction yield was about 95%.

EXAMPLE 10

Synthesis of ethyl(S)-4-chloro-3-hydroxybutyrate by the Carbonyl Reductase [2]

The reaction was carried out at 30 overnight in 1 ml of the reaction mixture containing 100 mM potassium phosphate buffer (pH 6.5), 1 mM $NAD^+$, 0.5 U of the carbonyl reductase obtained in Example 1, 2% ethyl 4-chloroacetoacetate, 1 U of glucose dehydrogenase (Wako Pure Chemical Industries, Ltd.), and 250 mM glucose. The formed ethyl 4-chloro-3-hydroxybutyrate was S-isomer with an optical purity of 99% ee or more. The yield of the reaction was about 95% (analyzed by the same method as in Example 9).

EXAMPLE 11

Analysis of Partial Amino Acid Sequence of the Carbonyl Reductase

The carbonyl reductase obtained in Example 1 was subjected to SDS-PAGE. A piece of gel containing the enzyme was cut out, washed twice with 0.2M $(NH_3)_2CO_3$, and then subjected to in-gel-digestion at 35 overnight using lysyl endopeptidase. The digested peptides were subjected to a reversed-phase HPLC (TSK gel ODS-80-Ts, 2.0 mm×250 mm, Tosoh Corporation), eluted with a gradient of acetonitrile solution in 0.1% trifluoroacetic acid (TFA), and fractionated.

Three kinds of the thus-obtained peptide fractions were named lep50_51, lep54, and lep59, and an amino acid sequence of each protein was determined by a protein sequencer (Hewlett Packard G1005A Protein Sequencer System). Amino acid sequences of Lep50_51, lep54, and lep59 are described in SEQ ID Nos: 3, 4, or 5, respectively.

EXAMPLE 12

Purification of the Chromosomal DNA from *Kluyveromyces aestuarii*

The *Kluyveromyces aestuarii* IFO 10597 strain was cultured in YM medium, and the cells were separated. The chromosomal DNA was purified from the cells according to the method described in Meth. Cell Biol. 29, 39–44 (1975).

EXAMPLE 13

Cloning of the Carbonyl Reductase Gene by PCR

Six kinds of sense primers and anti-sense primers were synthesized based on amino acid sequences lep50_51, lep54, and lep59. Nucleotide sequences are described in SEQ ID NO: 6 (KAR50-S), SEQ ID NO: 7 (KAR50-A), SEQ ID NO: 8 (KAR54-S), SEQ ID NO: 9 (KAR54-A), SEQ ID NO: 10 (KAR59-S), and SEQ ID NO: 11 (KAR59-A).

One sense primer and one anti-sense primer were paired to select a total of six primer pairs, and PCR was performed for 30 cycles in a reaction consisting of denaturation (94, 30 sec), annealing (45, 30 sec), and extension (70, 1 min), using GeneAmp PCR System 2400 (Perkin Elmer) in 50 L of the reaction mixture containing 50 pmol each primer, 10 nmol dNTP, 50 ng of the chromosomal DNA from *Kluyveromyces aestuarii*, the buffer for AmpliTaq (Takara Shuzo), and 2U AmpliTaq (Takara Shuzo).

A portion of the PCR reaction mixture was analyzed by agarose gel electrophoresis. As a result, putative specific bands were detected for the combinations of KAR50-S and KAR54-A, KAR50-S and KAR59-A, and KAR54-S and KAR59-A.

EXAMPLE 14

Subcloning of PCR Fragments of the Carbonyl Reductase Gene

The three DNA fragments obtained in Example 13 were extracted with phenol/chloroform and precipitated with ethanol to recover them as precipitates. Each of the DNA fragments was digested with BamHI and HindIII restriction endonucleases and subjected to agarose gel electrophoresis. A piece of agarose gel containing the target band was cut out, purified by SUPREC-01 (Takara Shuzo), and recovered as ethanol precipitates.

The DNA fragments thus obtained were ligated with plasmid pUC18, which was digested with BamHI and HindIII, using a Takara Ligation Kit, and *Escherichia coli* JM109 was then transformed with the ligated plasmid.

The transformants were grown on the LB plate (1% bacto-tryptone, 0.5% bacto-yeast extract, 1% NaCl) supplemented with ampicillin (50 g/mL), and the sizes of the inserted DNAs were confirmed by performing Colony Direct PCR for some grown colonies using M13-21 and M13-RP primers. The putative colonies harboring the target DNA fragments were cultured in LB liquid medium containing ampicillin, and the plasmids were then purified from the grown cells with Flexi-Prep (Pharmacia). The plasmids obtained by PCR using a combination of KAR50-S and KAR54-A, that of KAR50-S and KAR59-A, and that of KAR54-S and KAR59-A were named pKAR1, pKAR2, and pKAR3, respectively.

The purified plasmids were digested with BamHI and HindIII restriction endonucleases to confirm the sizes of the target inserts, followed by sequencing. Namely, the inserted DNAs were subjected to PCR using Dye Terminator Cycle Sequencing FS ready Reaction Kit (Perkin Elmer), and sequenced by DNA Sequencer 373A (Perkin Elmer). Nucleotide sequences of inserted fragments of pKAR1, pKAR2, and pKAR3 are described in SEQ ID NOs: 12, 13, and 14, respectively.

EXAMPLE 15

Subcloning DNA Near the Carbonyl Reductase Gene

The chromosomal DNA from *Kluyveromyces aestuarii* was digested with HaeII, and the digests were self-ligated at 16 overnight using T4 DNA ligase to circularize each DNA fragment. The circularized DNAs were subjected to PCR for 30 cycles of a reaction consisting of denaturation (94, 30 sec), annealing (55, 30 sec), and extension (70, 5 min) in 50 L of the reaction mixture containing 50 pmol each of primers KAR-5UP and KAR-3DN, 10 nmol of dNTP, 50 ng of the circularized DNAs, a buffer for Ex-Taq (Takara Shuzo), and 3U of Ex-Taq (Takara Shuzo) with GeneAmp PCR System 2400 (Perkin Elmer). A 9.5 kb fragment was detected by analyzing a portion of the PCR products by agarose gel electrophoresis.

The nucleotide sequences of primers KAR-5UP and KAR-3DNA are shown as SEQ ID NOs: 15 and 16, respectively. The amplified DNA fragments were recovered as ethanol precipitates after extraction with phenol/chloroform. After agarose gel electrophoresis, a piece of gel containing the target band was cut out and purified using EASYTRAP Ver.2 (Takara Shuzo).

The thus-obtained DNA fragments were ligated with pT7Blue T-vector (Novagen) using Takara Ligation Kit ver. 2, and *E. coli* JM109 was transformed with the ligated plasmids. The transformants were grown on the LB plate (1% bacto-tryptone, 0.5% bacto-yeast extract, 1% NaCl) supplemented with 50 g/mL of ampicillin, 50 g/mL of 5-bromo-4-chloro-3-indolyl-D-galactopyranoside, and 20 g/mL of isopropylthio-D-galactopyranoside (IPTG). The sizes of the inserted fragments were confirmed by performing Colony Direct PCR for several white colonies using KAR-3DN and KAR-5UP as primers. The putative colonies harboring the target DNA fragments were cultured in LB liquid medium containing ampicillin; the plasmids were then purified from the grown cells with Flexi-Prep (Pharmacia). The plasmids thus obtained were named pT7B-F3 and pT7B-F8.

The nucleotide sequences of the inserted DNAs were analyzed by the primer-walking method. The nucleotide sequence was determined by PCR using Dye Terminator Cycle Sequencing FS Ready Reaction Kit (Perkin Elmer) and by DNA Sequencer 373A (Perkin Elmer).

The nucleotide sequence inserted into pKAR2 with its 5'-upstream and 3'-downstream sequences was synthesized and shown in SEQ ID NO: 17. The sequence of the carbonyl reductase (KaCR1) was determined by ORF search in the nucleotide sequence represented by SEQ ID NO: 17. The determined nucleotide sequence and the deduced amino acid sequence are shown in SEQ ID NO: 1 and SEQ ID NO: 2, respectively. The above synthesis of the nucleotide sequence and OFR search were performed using Genetyx ATSQ, and Genetyx (Software Development Co., Ltd.).

EXAMPLE 16

Cloning the Carbonyl Reductase Gene

KAR-ORF5 (SEQ ID NO: 18) and KAR-ORF3 (SEQ ID NO: 19) primers for cloning were synthesized based on the nucleotide sequence of the structural gene of the carbonyl reductase. The chromosomal DNA from *Kluyveromyces aestuarii* was subjected to PCR for 30 cycles of a reaction consisting of denaturation (95", 30 sec), annealing (50", 1 min), and extension (75", 5 min) in 50" 1 of the reaction mixture containing 50 pmol of each primer, 10 nmol of dNTP, 50 ng of the chromosomal DNA from *Kluyveromyces aestuarii*, 2U of Pfu-DNA polymerase, and a buffer for the enzyme (STRATAGENE) using GeneAmp PCR System 2400 (Perkin Elmer).

The putative specific bands were observed by analyzing a portion of PCR products by agarose gel electrophoresis.

The amplified DNA fragments were recovered as ethanol precipitates after extraction with phenol/chloroform. The DNA fragments were digested with BamHI and XbaI and were subjected to agarose gel electrophoresis. A piece of agarose gel containing targeted bands was then cut out, and the DNAs were recovered as ethanol precipitates after purification using SUPREC-01 (Takara Shuzo).

The thus-obtained DNA fragments were ligated into plasmid pSE420 (Invitrogen), which was digested with BamHI and XbaI, using a Takara Ligation Kit, and the resulting plasmids were introduced into *Escherichia coli* JM109.

The transformants were grown on the LB plate containing ampicillin (50 "g/mL), and the sizes of the inserted fragments were confirmed by performing Colony Direct PCR for several grown colonies using Trc-3b and Trc-5b (SEQ ID NOs: 20 and 21) as primers. The putative colonies harboring the target DNA fragment were incubated at 30" overnight in LB liquid medium containing ampicillin; cultivation was then continued for four more hours after the addition of 0.1 mM IPTG to the culture medium.

The cells were harvested by centrifugation then suspended in 50 mM potassium phosphate buffer (pH 6.5) containing 0.02% 2-mercaptoethanol, 2 mM PMSF, and 0.5 M NaCl and disrupted by sonication for 3 min using a sealed ultrasonic cell disrupter (UCD-200™ (Cosmo Bio)). The resulting suspension was then centrifuged to obtain the supernatant as cell extracts. The cell extracts were reacted with ethyl 4-chloroacetoacetate to measure the reductase activity to the substrate.

The transformants capable of expressing the highest activity were cultured in the liquid LB medium containing ampicillin (50 "g/mL). The plasmid was purified from the transformants using Qiagen 500 (Qiagen) and named plasmid pSE-KAR1. The nucleotide sequence of the inserted DNA in the plasmid was determined by PCR using a Dye Terminator Cycle Sequencing FS Ready Reaction Kit (Perkin Elmer) and DNA Sequencer 373A (Perkin Elmer).

Figure 6:
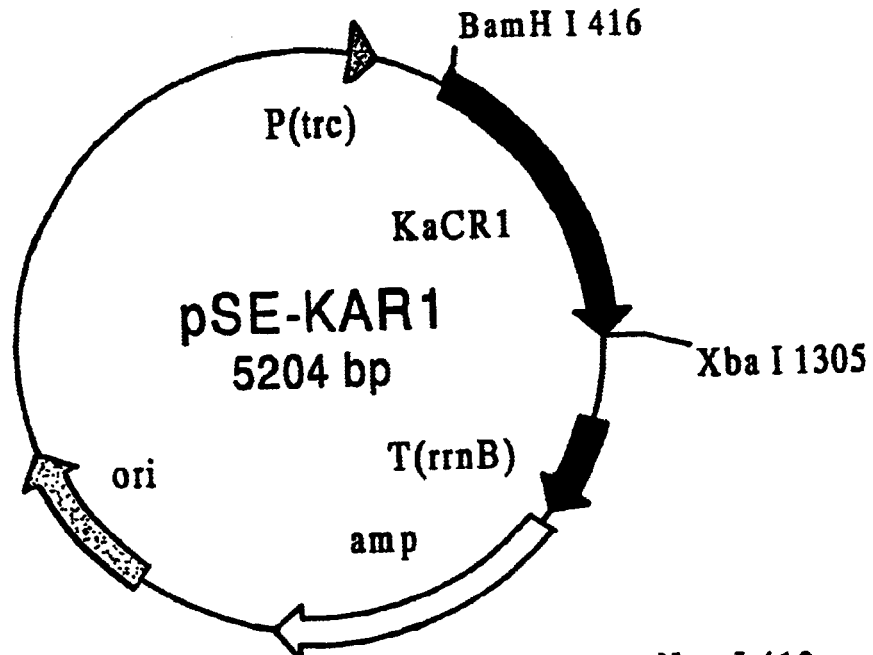
FIG. 6 illustrates the restriction map of plasmid pSE-KAR1 constructed in Example 16.

The inserted DNA fragment was the same sequence as that of KaCR1 represented by SEQ ID NO: 1 with 5'-upstream 12 base pairs that were attached for cloning. The nucleotide sequence of the inserted DNA fragment in plasmid pSE-KAR1, the amino acid sequence of the coding sequence, and a restriction map of the plasmid are shown in SEQ ID NO: 22, SEQ ID NO: 23, and FIG. 6, respectively. *E. coli* transformed with the control plasmid pSE420 (not harboring the insert) was cultured overnight in LB medium. After 0.1 mM IPTG was added, cultivation was continued for an additional 4 hours, and the cells were disrupted in the same manner as described above. The reductase activity of the cell extract to ethyl 4-chloroacetoacetate was assayed, but not detected.

EXAMPLE 17

Synthesis of ethyl(S)-4-chloro-3-hydroxybutyrate by the Recombinant Carbonyl Reductase Ethyl(S)-4-chloro-3-hydroxybutyrate was produced from ethyl 4-chloroacetoacetate using the cell extract prepared in Example 16. The reaction was performed at 25" overnight in 1 ml of the reaction mixture containing 100 mM potassium phosphate buffer (pH 6.5), 1 mM NAD$^+$, 1.0U of the recombinant carbonyl reductase, 2% ethyl 4-chloroacetoacetate, 2 U of glucose dehydrogenase (Wako Pure Chemical Industries), and 250 mM glucose. The formed ethyl(S)-4-chloro-3-hydroxybutyrate was S-isomer with an optical purity of 98.4% ee or more, and the yield was about 99% (measured by the same methods as in Example 9).

EXAMPLE 18

Purification of the DNA from *Bacillus subtilis*

*Bacillus subtilis* BGSC 1A1 strain was cultured on LB medium, and the cells were harvested. The chromosomal DNA was purified from the cells using Qiagen Genomic Tip (Qiagen) according to the method described in the appendix.

EXAMPLE 19

Construction of Plasmid pSE420D for Coexpression

Figure 7:
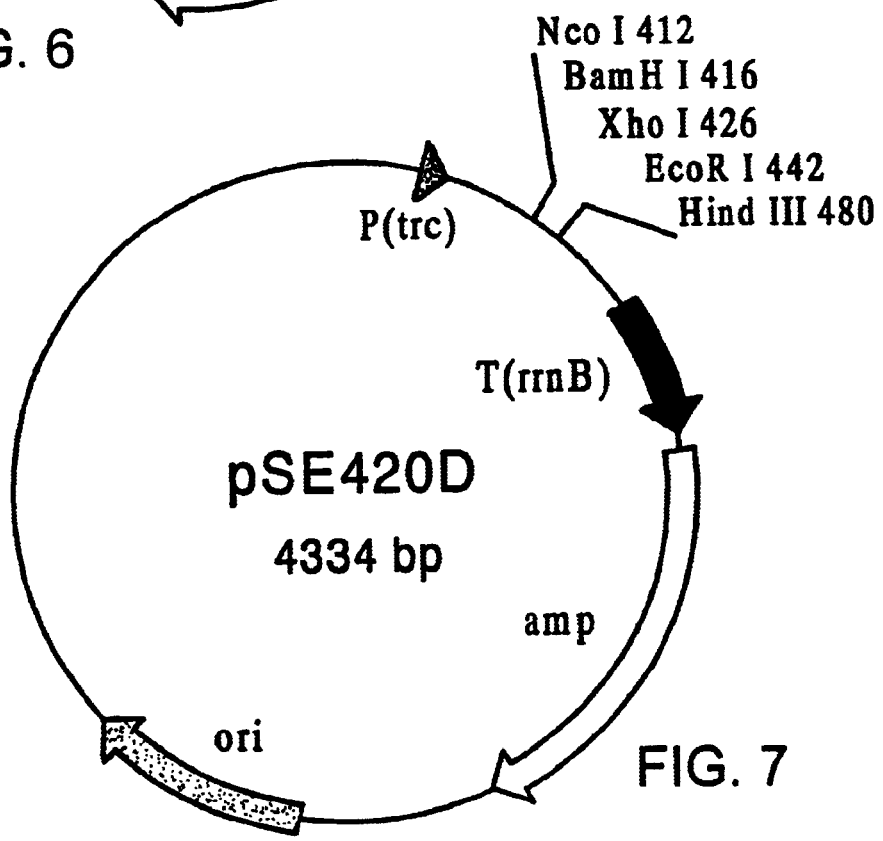
FIG. 7 illustrates the restriction map of plasmid pSE420D constructed in Example 19.

Plasmid vector pSE420 (Invitrogen) was digested with NcoI and BamHI, treated with Klenow fragment, and self-circularized to construct plasmid pSE420B. Synthetic DNAs SE420D-S described in SEQ ID NO: 24 and SE420D-A described in SEQ ID NO: 25 were annealed and ligated into plasmid pSE420B, which was digested using MunI and SpeI, with T4 DNA ligase, thereby obtaining plasmid pSE420D. A restriction map of plasmid pSE420D is shown in FIG. 7.

EXAMPLE 20

Cloning of Glucose Dehydrogenase Gene from *Bacillus subtilis*

A glucose dehydrogenase gene, which is to be used for regenerating NADPH, was cloned from *Bacillus subtilis* by a known method (J. Bacteriol. 166, 238–243 (1986)).

Primers BSG-ATG1 (SEQ ID NO: 26) and BSG-TAA2 (SEQ ID NO: 27) were synthesized based on 5'- and 3'-sequences of the structural gene of the sequence of the glucose dehydrogenase gene described in the above reference, to clone only the open reading frame by PCR. PCR was performed for 30 cycles (95", 30 sec; 50", 1 min; 75", 3 min 15 sec), using the chromosomal DNA from *Bacillus subtilis* prepared in Example 18 as a template to obtain amplified DNAs.

Figure 8:
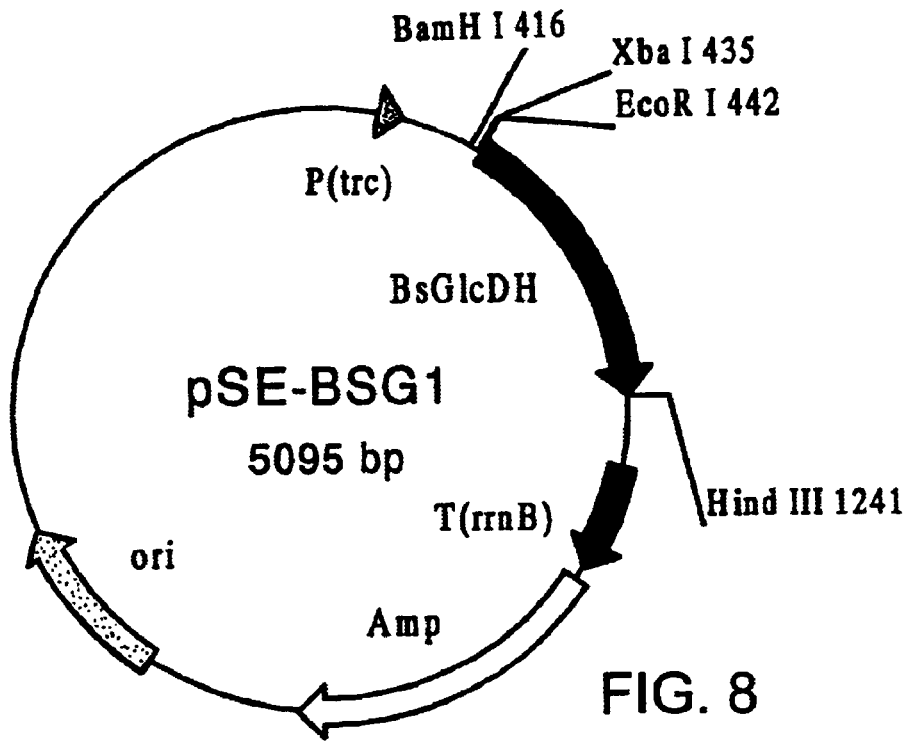
FIG. 8 illustrates the restriction map of plasmid pSE-BSG1 constructed in Example 20.

The amplified DNA fragments were digested with EcoRI and HindIII, and ligated into a plasmid vector, pSE420D, which was digested using EcoRI and HindIII, with T4 DNA ligase to obtain plasmid pSE-BSG1. A restriction map of the plasmid is illustrated in FIG. 8. The determined nucleotide sequence of the inserted DNA fragment agreed with the nucleotide sequence registered in the database (DDBJ Accession No. M12276). The thus-obtained nucleotide sequence of the glucose dehydrogenase gene and amino acid sequence of the protein encoded by the gene are shown in SEQ ID NO: 28 and SEQ ID NO: 29.

EXAMPLE 21

Construction of Plasmid pSG-KAR1 Coexpressing the Carbonyl Reductase from *Kluyveromyces aestuarii* and Glucose Dehydrogenase from *Bacillus subtilis*

The DNA fragments containing a gene encoding the carbonyl reductase from *Kluyveromyces aestuarii* were prepared by digesting plasmid pSE-KAR1 constructed in Example 16 with BamHI and XbaI.

The plasmid pSE-KAR1 containing the carbonyl reductase gene from *Kluyveromyces aestuarii* was digested with BamHI and XbaI. It was then ligated with plasmid pSE-BSG1 from Example 20 containing the *Bacillus subtilis*-derived glucose dehydrogenase gene, which was digested with BamHI and XbaI, with T4 DNA ligase to obtain the plasmid pSG-KAR1. This plasmid (pSG-KAR1) can express glucose dehydrogenase and "-ketoacyl-ACP reductase simultaneously.

Figure 9:
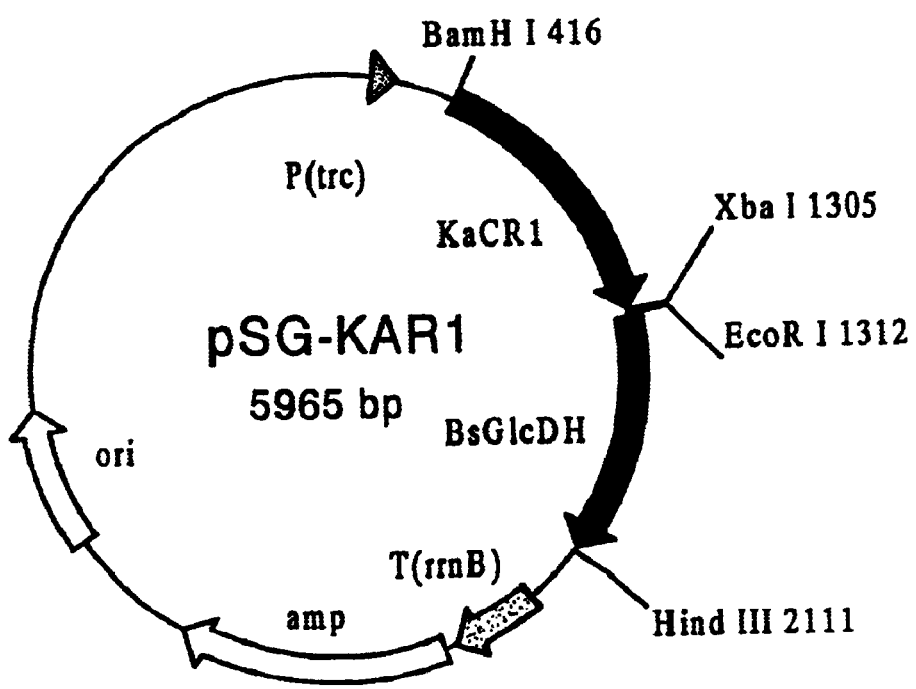
FIG. 9 illustrates the restriction map of plasmid pSG-KAR1 constructed in Example 21.

A restriction map of plasmid pSG-KAR1 is illustrated in FIG. 9.

EXAMPLE 22

Coexpression of the Glucose Dehydrogenase Derived from *Bacillus subtilis* and the Carbonyl Reductase Derived from *Kluyveromyces aestuarii* in *E. coli*

*E. coli* JM109, HB101, TG1, and W3110 were transformed with plasmid pSG-KAR1 that can coexpress the glucose dehydrogenase from *Bacillus subtilis* and the carbonyl reductase from *Kluyveromyces aestuarii*.

Each recombinant *E. coli* strain was cultured at 30" overnight in the LB liquid medium. After 0.1 mM IPTG was added, the culture medium was cultivated for an additional 4 hours. The cells were harvested from each of the four transformants to measure their enzyme activities and subject them to the reduction reaction of ethyl 4-chloroacetoacetate.

EXAMPLE 23

Enzyme Activities of *E. coli* Strains Transformed with pSG-KAR1

The grown cells (1.5 mL of the culture) of *E. coli* transformed with plasmid pSG-KAR1 prepared in Example 22 were disrupted by the method described in Example 16, and the cell extract was prepared to assay its enzyme activities. The enzymatic reaction for assaying the glucose dehydrogenase activity was performed at 25" in a reaction mixture containing 100 mM potassium phosphate buffer (pH 6.5), 2.5 mM $NAD^+$, 100 mM D-glucose, and the enzyme. One unit of the enzyme is defined as the amount capable of catalyzing the formation of 1 "mol NADH in 1 min under conditions described above. Each enzyme activity of the crude enzyme solution from each recombinant *E. coli* is shown in Table 4.

TABLE 4

Enzyme activities of *E. coli* transformed with pSG-KAR1

| Host | Enzyme activity | |
|---|---|---|
| | Glc-DH | ECAA-R |
| JM109 | 2.19 | 3.66 |
| HB101 | 3.42 | 2.70 |
| TG1 | 3.51 | 2.81 |
| W3110 | 3.44 | 3.82 |

Enzyme activity: enzyme activity/1 ml culture
Glc-DH: glucose dehydrogenase activity
ECAA-R: reductase activity to ethyl 4-chloroacetoactate

EXAMPLE 24

Synthesis of ethyl(S)-4-chloro-3-hydorxybutyrate using *E. coli* Transformed with pSG-KAR1

*E. coli* HB101, TG1, and W3110 transformed with plasmid pSG-KAR1 prepared in Example 23 were cultured in LB liquid medium at 30" overnight. Each preculture was inoculated into 2×YT medium (Bacto-Tryptone 20 g, Bacto-Yeast extract 10 g, NaCl 10 g/L) and grown at 37" for 4 hours. After 0.1 mM IPTG was added, the cultured medium was cultivated for an additional 4 hours. The grown cells were collected, and their reductase activity to ethyl 4-chloroacetoacetate was measured.

The enzyme reaction was performed at 25" overnight with shaking in 20 ml of a reaction mixture containing the *E. coli* cells prepared from 20 ml of the cultured medium, 200 mM potassium phosphate buffer (pH 6.5), 5% ethyl 4-chloroacetoacetate, 607 mM D-glucose, and 1 mM $NAD^+$. Separately, the reaction was performed under the same conditions described above but without $NAD^+$. The amount of ethyl(S)-4-hydorxybutyrate and its purity were determined in the same manner described in Example 9, and the results are shown in Table 5.

TABLE 5

Synthesis of SECHB using *E. coli* transformed with pSG-KAR1

| Host | $NAD^+$ added | | $NAD^+$ not added | |
|---|---|---|---|---|
| | (g/L) | % ee(s) | (g/L) | % ee(s) |
| HB101 | 42.3 | 99.0 | 13.2 | 99.9 |
| TG1 | 42.5 | 99.4 | 19.3 | 99.9 |
| W3110 | 49.9 | 99.9 | 23.0 | 99.9 |

SECHB: ethyl (S)-4-chloro-3-hydroxybutyrate

What is claimed is:

1. A purified carbonyl reductase having the following physicochemical properties:

reduces 4-haloacetoacetate ester to produce (S)-4-halo-3-hydroxybutyrate ester using reduced β-nicotinamide ademne dinucleotide as an electron donor;

has high reductase activity for 4-chloroacetoacetate ester but does not substantially dehydrogenate any optical isomers of 4-halo-3-hydroxybutyrate ester;

shows higher enzymatic activity when used with reduced β-nicotinamide adenine dinucleotide as an electron donor than when used with reduced β-nicotinamide adenine dinucleotide phosphate;

has an optimal pH of 5.0 to 6.0;

does not substantially dehydrogenate isopropanol and does not reduce acetoacetate; and has a molecular weight of about 32,000 daltons when determined by sodium dodecylsulfate-polyacrylamide gel electrophoresis;

wherein the carbonyl reductase is a *Kluyveromyces aestuarii* carbonyl reductase.

* * * * *